United States Patent
Vedrine et al.

(10) Patent No.: US 11,226,331 B2
(45) Date of Patent: Jan. 18, 2022

(54) CONTROLS FOR IMPLEMENTING MULTIPLEX ANALYSIS METHODS

(71) Applicant: BIO-RAD EUROPE GMBH, Basel (CH)

(72) Inventors: Christophe Rene Roger Vedrine, Courbevoie (FR); Nadine Marie Renee Lambert, Chatou (FR)

(73) Assignee: BIO-RAD EUROPE GMBH, Basel (CH)

( * ) Notice: Subject to any disclaimer, the term of this patent is extended or adjusted under 35 U.S.C. 154(b) by 103 days.

(21) Appl. No.: 15/301,884

(22) PCT Filed: Apr. 3, 2015

(86) PCT No.: PCT/EP2015/097005
§ 371 (c)(1),
(2) Date: Oct. 4, 2016

(87) PCT Pub. No.: WO2015/150583
PCT Pub. Date: Oct. 8, 2015

(65) Prior Publication Data
US 2017/0030901 A1 Feb. 2, 2017

(30) Foreign Application Priority Data
Apr. 4, 2014 (FR) ..................................... 1453038

(51) Int. Cl.
*B01L 3/00* (2006.01)
*G01N 33/543* (2006.01)

(52) U.S. Cl.
CPC . *G01N 33/54306* (2013.01); *G01N 33/54326* (2013.01); *G01N 33/54366* (2013.01)

(58) Field of Classification Search
CPC ....... G01N 33/54306; G01N 33/54366; G01N 33/5302; G01N 33/54326
USPC ........................................ 422/552, 105, 553
See application file for complete search history.

(56) References Cited

U.S. PATENT DOCUMENTS

| | | | |
|---|---|---|---|
| 4,318,707 A | 3/1982 | Litman et al. | |
| 5,082,768 A | 1/1992 | Burd et al. | |
| 5,811,312 A | 9/1998 | Hasegawa et al. | |
| 2001/0006820 A1 | 7/2001 | Knapp et al. | |

(Continued)

FOREIGN PATENT DOCUMENTS

| | | |
|---|---|---|
| JP | 2004-500569 | 1/2004 |
| JP | 2010-511177 | 4/2010 |

(Continued)

OTHER PUBLICATIONS

Ferbas, J. et al. "Feasibility of a Multiplex Flow Cytometric Bead Immunoassay for Detection of Anti-Epoetin Alfa Antibodies" *Clinical and Vaccine Immunology*, Sep. 2007, pp. 1165-1172, vol. 14, No. 9.

(Continued)

*Primary Examiner* — Natalia Levkovich
(74) *Attorney, Agent, or Firm* — Saliwanchik, Lloyd & Eisenschenk

(57) ABSTRACT

The present invention relates to controls which may be used to secure the results of multiplex analysis methods. The present invention thus relates to solid supports comprising one or several controls and their use in multiplex analysis methods to detect several analytes potentially present in a sample.

12 Claims, 5 Drawing Sheets

(56) References Cited

U.S. PATENT DOCUMENTS

Figure 1:
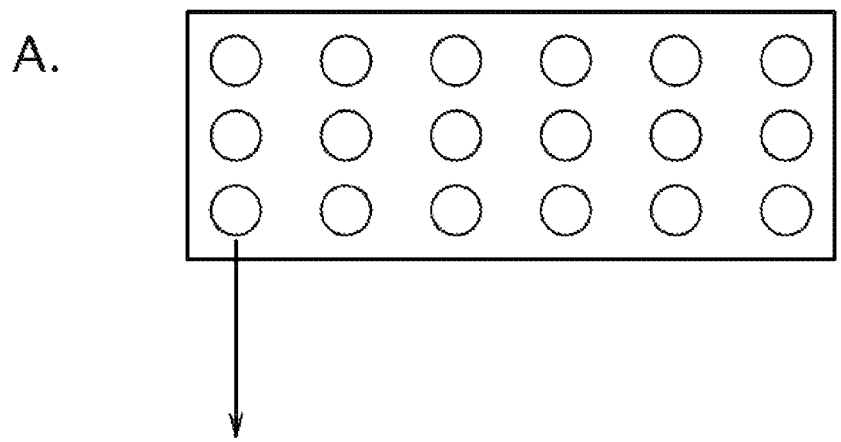
Figure 1:
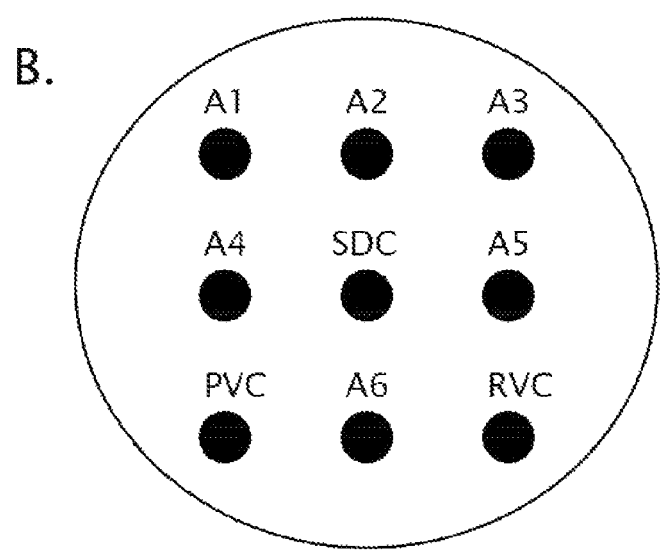
Figure 1:
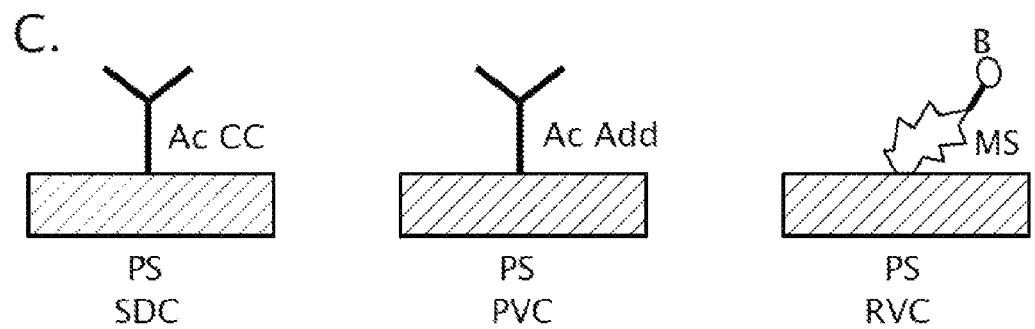

| | | | |
|---|---|---|---|
| 2006/0063197 | A1 | 3/2006 | Anderson et al. |
| 2007/0202538 | A1* | 8/2007 | Glezer .................. B01L 3/5025 435/7.1 |
| 2007/0231922 | A1* | 10/2007 | Petruno .............. G01N 21/8483 436/514 |
| 2009/0068162 | A1 | 3/2009 | Sack et al. |
| 2010/0267071 | A1 | 10/2010 | Akhavan-Tafti et al. |
| 2012/0196767 | A1 | 8/2012 | Cooney et al. |
| 2013/0040834 | A1* | 2/2013 | Bunce .................. B01L 3/5085 506/9 |

FOREIGN PATENT DOCUMENTS

| | | |
|---|---|---|
| JP | 2012-100679 | 5/2012 |
| JP | 2014-501497 | 1/2014 |
| WO | WO 01/63284 | 8/2001 |
| WO | WO 03/022028 | 3/2003 |
| WO | WO 2008/067091 | 6/2008 |
| WO | WO 2012/055069 | 5/2012 |
| WO | WO 2015/155248 | 10/2015 |
| WO | WO 2015/155254 | 10/2015 |
| WO | WO 2015/155255 | 10/2015 |

OTHER PUBLICATIONS

Schuchhardt, J. et al. "Normalization strategies for cDNA microarrays" *Nucleic Acids Research*, 2000, pp. 1-5, vol. 28, No. 10.

Werling, D. et al. "Ability to differentiate between cp and nep BVDV by microarrays: Towards an application in clinical veterinary medicine?" *Veterinary Immunology and Immunopathology*, 2005, pp. 157-164, vol. 108.

Wilson, W. J. et al. "A multiplexed PCR-coupled liquid bead array for the simultaneous detection of four biothreat agents" *Molecular and Cellular Probes*, 2005, pp. 137-144, vol. 19, No. 2.

Auld, D. S. et al. "Characterization of Chemical Libraries for Luciferase Inhibitory Activity" *J. Med. Chem*, 2008, pp. 2372-2386, vol. 51, No. 8.

Petersen, J. et al. "Comparison of Absorbance and Fluorescence Methods for Determining Liquid Dispensing Precision" *JALA*, Apr. 2005, pp. 82-87, vol. 10.

Linares, E. M. et al. "Enhancement of the detection limit for lateral flow immunoassays: Evaluation and comparison of bioconjugates" *Journal of Immunological Methods*, 2012, pp. 264-270, vol. 375.

Gao, H. et al. "Amorphous carbon nanoparticle used as novel resonance energy transfer acceptor for chemiluminescent immunoassay of transferrin" *Analytica Chimica Acta*, 2014, pp. 102-107, vol. 819.

Dodeigne, C. et al. "Chemiluminescence as diagnostic tool. A review" *Talanta*, 2000, pp. 415-439, vol. 51.

SIRS-Lab Gmbh, "Lab Arraytor® human 60-inflammation, Technical Manual", Jan. 1, 2006, Protocol No. 1, Version No. 2006-1, pp. 1-44.

Kersten, B. et al. "Multiplex approaches in protein microarray technology" *Expert Reviews of Proteomics*, 2005, pp. 499-510, vol. 2, No. 4.

* cited by examiner

CONTROLS FOR IMPLEMENTING MULTIPLEX ANALYSIS METHODS

CROSS-REFERENCE TO RELATED APPLICATION

This application is the U.S. national stage application of International Patent Application No. PCT/EP2015/097005, filed Apr. 3, 2015.

TECHNICAL FIELD

The present invention relates to controls able to be used to secure the results of multiplex analysis methods comprising one or several steps.

BACKGROUND OF THE INVENTION

A multiplex analysis method allows the simultaneous detection of the potential presence of several analytes within a same sample. Multiplex analysis has several advantages, such as time savings by making it possible to analyze several analytes at the same time, lower consumption of reagents and consumables, as well as a lower quantity sample needed to detect analytes.

It is common to use one or several controls to validate the results obtained at the end of the analysis method seeking to detect the presence of one or several analytes. The reliability of the results provided by an analysis device is in fact a major issue, in particular when it involves analyses intended for medical diagnostics and/or the qualification of transfusion donations.

One positive control traditionally used consists of verifying the detection of a known compound, used in a known quantity and that corresponds to an analyte whereof the potential presence is sought in a given sample. However, this type of control makes it possible to validate only the overall implementation of the analysis method and does not make it possible to validate each step of the method.

Furthermore, other types of control may be used. For example, document WO2004/046685 uses controls to verify the quality of the reagents used in immuno-histochemical tests. To that end, a controlled slide comprising a series of solutions of different control compounds is used. Positive coloring of the control side at a control compound must only be observed if a specific antibody of said control compound or a reporter or substrate of said control compound is used during the immuno-marking method. This method for verifying the quality of the reagents requires the use of a large number of control compounds on the control slide.

Indeed, there is currently no simple means making it possible to control all of the steps in the case of a multiplex analysis method: in particular, the deposition of the sample, the deposition of the reagents, the different water and incubation cycles. It is, however, crucial in the field of blood transfusions and medical diagnostics to achieve a high level of security and traceability.

Thus, there is a real need to provide solutions making it possible to guarantee the reliability of the results obtained during the implementation of multiplex analysis method and that in particular make it possible to validate each step of the method.

DETAILED DESCRIPTION OF THE INVENTION

The present invention is based on the revelation by the inventors of control means making it possible to guarantee the reliability of the obtained results, by verifying that each step of a multiplex analysis method has taken place correctly (and not by only verifying an overall implementation of the method). Thus, for the first time, the inventors are providing controls that make it possible to validate the deposition of the sample itself, and more generally the different steps of the method.

By combining only two or three controls according to the invention, it is thus possible to validate the deposition step of the sample, the deposition step(s) of the specific detection ligands of the analytes to be detected in the sample, the different washing and incubation steps, and if applicable, the deposition step of a reporter of a detection marker and/or the deposition step of a substrate of the marker coupled to said reporter.

In the multiplex analysis method according to the invention, only two or three controls are necessary to validate each step of the entire multiplex method.

Aside from the validation of the results, the use of the controls according to the invention also makes it possible to identify potential faults existing during the implementation of the multiplex analysis method, and for example to modify the corresponding step(s) to improve the implementation of the analysis method.

The present invention also has the advantage of being easy to implement, requiring only a limited number of controls, not adding additional steps to the analysis method and not requiring the use of additional equipment (for example, not requiring the use of a spectrophotometer). Indeed, the steps of the analysis method are done in a single location (for example, the tube with the well in which the sample is placed) and the controls, for example in the form of spots or beads, are processed at the same time as the spots or beads used to detect analytes.

The first type of control according to the invention is the control of the deposition of a sample that makes it possible to verify the deposition of the sample. In certain embodiments outlined below, the control of the deposition of the sample also makes it possible to verify the deposition of one or several analyte detection ligands.

"Deposition of the sample or an additive" or "addition of the sample or an additive" refers to the placement of the sample or at least one additive in the presence of the compounds of interest fixed on a solid support.

"At least one", within the meaning of the present application, refers to one or several, several in particular meaning two, three, four, five, six, seven, eight, nine, ten, eleven, twelve, thirteen, fourteen, fifteen, sixteen or more than sixteen.

"Deposition of a detection ligand, a reporter or a substrate" or "addition of a detection ligand, a reporter or a substrate" refers to the placement of a detection ligand, a reporter or a substrate in the presence of compounds of interest fixed on a solid support and any compounds fixed on said compounds of interest.

The second type of control is the control of the deposition of a detection ligand of an analyte that makes it possible to verify the deposition of one or more specific detection ligands (for example a mixture of detection ligands) of analytes to be detected in the sample. This control also makes it possible to validate the incubation and washing steps.

The third type of control is the control of the deposition of a reporter that makes it possible to verify that the developing step(s) have taken place correctly. The control of the deposition of a reporter is useful in case of indirect marking of the detection ligands.

Lastly, the controls according to the invention are particularly appropriate for carrying out multiplex analysis methods in micro-arrays, for example on a solid support of the microplate type, or in liquid chip, for example on a solid support of the bead type.

Sample

The sample to be analyzed is preferably a biological sample.

The biological sample may be a biological fluid, such as a sample of blood, blood derivatives (such as plasma or serum), urine, cerebrospinal fluid, saliva, or a tissue sample, such as a tissue obtained by biopsy, a cell or set of cells, a plant extract, or combinations thereof.

A blood derivative refers to any product, in particular fluid, obtained from a blood sample.

The sample to be analyzed may also be a culture medium and/or a culture supernatant.

Before being analyzed, the sample may undergo one or several prior treatment steps, such as dilution, centrifugation, heat and/or chemical treatment, cell lysis (for example by one or several chaotropic agents, one or several reducing agents and/or by heating), extraction, PCR (Polymerase Chain Reaction), addition of an unmarked detection ligand or combinations thereof. The addition of an unmarked detection ligand is in particular useful to implement a neutralization test, which in itself is a test known by those skilled in the art.

The sample may also be a mixture of at least two samples that may be of the same nature or different natures.

Examples of mixtures of samples of different natures are a mixture of blood and serum, a mixture of blood and plasma, a mixture of serum and plasma, or a mixture of blood, serum and plasma.

One preferred sample according to the invention is a sample or mixture of samples of blood and/or blood derivatives.

Analyte

An analyte to be detected in a sample may be any type of compound, natural or synthetic, that one wishes to detect and/or quantify in a sample.

An analyte may for example be a protein, a peptide, a glycoprotein, a carbohydrate, a lipid, a cell, an organelle, a virus or a nucleic acid.

The cell may be an animal cell, a plant cell, a bacteria cell, a protozoa, a metazoan cell, a yeast cell, a fungus cell or a protozoa.

A nucleic acid designates a polymer of nucleotides linked by phosphodiester bonds, such as a deoxyribonucleic acid (DNA), a ribonucleic acid (RNA) or an analogue thereof, such as phosphorothioates or thioesters, in single-strand or double-stranded form.

An analyte or at least one of the analytes or the analytes is (are) for example chosen from the group consisting of an antigen, an antibody, an antibody fragment, a hapten, a hormone, a hormone receptor, an enzyme, or a nucleic acid.

In one preferred embodiment, the analyte(s) are not nucleic acids.

The analyte(s) are for example selected from the group consisting of an antigen, an antibody, an antibody fragment, a hapten, a hormone, a hormone receptor and an enzyme.

Here, "antigen" refers to a natural, recombinant or synthetic molecule recognized by antibodies or cells of the immune system and capable of causing an immune response when it is presented under appropriate conditions to the immune system of a host. This may be a molecule, in particular a polypeptide, comprising or consisting of at least one epitope that may be linear or conformational. The term "linear epitope" refers to a polypeptide, in particular a peptide, comprising or generally consisting of 3 to 15, more generally 5 to 15 amino acids, preferably at least 6, 8, 10 or 12 amino acids, capable of binding to an antibody molecule against said antigen. The term "conformational epitope" refers to a three-dimensional structure recognized by an antibody and determined by the juxtaposition of several amino acids in space, which may be noncontiguous in the peptide sequence of the protein (or polypeptide) against which this antibody is directed, but which, due to the folding of the polypeptide chain, find themselves dose to one another in space, and can thus form a pattern that may be recognized by an antibody.

An antigen is for example a protein (in particular a native or recombinant protein), a peptide (for example, a synthetic peptide), a glycoprotein, a carbohydrate or a lipid, said peptide being able to be associated or not associated with a carrier molecule, for example BSA (bovine serum albumin).

In the present application, a "carrier molecule" in particular refers to a protein or carbohydrate carrier molecule. A carrier molecule may be a polypeptide (in particular protein or a peptide), which may or may not be natural (for example, a recombinant protein or a synthetic peptide), a functionalized polymer (such as dextran, polysaccharide or polylysine) or a mixed copolymer (in particular a copolymer of different amino acids, for example a lysine-tyrosine copolymer). A carrier molecule may be an antibody (in particular a monoclonal antibody or a polyclonal antibody), for example an immunoglobulin.

One example carrier molecule is BSA.

In one specific embodiment, the carrier molecule is not an antibody.

"Hapten" here refers to a molecule with a low molecular weight capable of being recognized by the immune system, but which is immunogenic only when it is coupled to a carrier molecule.

An analyte or at least one of the analytes is preferably a compound making it possible to diagnose a condition in a subject, which may or may not be pathological, or to diagnose the risks of developing a condition, which may or may not be pathological. An example of a non-pathological condition is a pregnancy.

The subject may be a human, a non-human animal or a plant. The non-human animal is preferably a mammal, such as a cat, dog, monkey, rabbit, mouse or rat.

The term "human" is used broadly and in particular designates a man or a woman of any age, such as an infant, a child, an adolescent, an adult or an elderly person.

When the analyte or at least one of the analytes is an antigen, it is preferably an antigen making it possible to diagnose an infection, for example an infection caused by a virus, a bacteria, a fungus or a parasite.

When the analyte or at least one of the analytes is an antibody, it is preferably an antibody making it possible to diagnose an infection, for example an infection caused by a virus, a bacteria, a fungus or a parasite.

Typically, this may involve one or several antigens and/or one or several antibodies of:
  a virus, such as HIV (Human Immunodeficiency Virus), in particular HIV-1 or HIV-2, HBV (Hepatitis B Virus), HCV (Hepatitis C Virus), HPV (Human Papilloma Virus), HTLV (Human T-Lymphotropic Virus), in particular HTLV-I or HTLV-II,
  a parasite, such as a parasite that may cause toxoplasmosis (in particular *Toxoplasma gondii*), malaria (in particular a parasite of the *Plasmodium* genus, for example *Plasmodium falciparum, Plasmodium vivax, Plasmo-*

*dium ovale, Plasmodium malariae* or *Plasmodium knowlesi*) or Chagas disease (in particular *Trypanosoma cruzi*) in humans or non-human animals, or a bacteria, such as a bacteria able to cause syphilis (*Treponema pallidum*) or Lyme disease (in particular a bacteria from the *Borrelia* genus) in humans or non-human animals.

"Parasite" here refers to a metazoan or a protozoa acting as parasite with respect to a body and causing parasitosis. A parasite within the meaning of the invention is therefore not a virus, a bacteria or a fungus.

The analyte or at least one of the analytes may also be a marker for disease, such as a marker of a cardiovascular disease or a diabetes marker, a marker of the evolution of the disease, such as hepatitis, a marker of the evolution of an infection caused by a virus, a bacteria, a fungus or a parasite, a marker of resistance to a treatment, for example to an antiviral treatment, an antibiotic treatment or a cancer treatment.

Several (for example, two, three, four, five, six, seven, eight, nine, ten, eleven, twelve, thirteen, fourteen, fifteen or more than fifteen) analytes as described in the present application may be detected simultaneously in a sample during a multiplex analysis method. This may make it possible to diagnose, in a same sample, one or several infections or diseases, the evolution of an infection or disease, a condition (pathological or not), a risk of developing a condition (pathological or not) or a marker of resistance to a treatment in a subject.

The analytes detected during a multiplex analysis method may be of the same nature (for example only antibodies or only) or of different natures (for example, at least one antigen and at least one antibody).

Preferably, the analyte(s) to be detected are not marked with a detection marker.

In one preferred embodiment, the analyte(s) to be detected are chosen from among an antibody and/or an antigen.

Control Compound

Here, "control compound" refers to a compound naturally present in the sample to be analyzed, preferably at a concentration detectable in all of the samples of the same nature.

The compound naturally present in the sample to be analyzed can be a compound initially present in the sample or a derivative of a compound initially present in the sample.

A derivative of a compound initially present in the sample can be obtained at the end of one or several treatment steps of the sample prior to the analysis method. These steps are in particular as defined above, for example heat and/or chemical treatment, cell lysis, extraction, PCR (Polymerase Chain Reaction), addition of an unmarked detection ligand or combinations thereof.

A derivative of a compound initially present in the sample is for example a PCR product and/or a compound modified by a heat and/or chemical treatment, cell lysis, the addition of an unmarked detection ligand or combinations thereof.

Preferably, a compound naturally present in the sample to be analyzed is a compound initially present in the sample. In this case, if one or several treatment steps of the sample prior to the analysis method are carried out, the compound is therefore present before any prior treatment step of the sample.

A compound naturally present in the sample to be analyzed does not include a compound present in the sample at the time of the analysis, but that has been added or that is derived from a compound added to the sample during one or several prior treatment steps of the sample.

When the sample is a mixture of at least two samples, the control compound is a compound naturally present in at least one of said samples, preferably in each sample of the mixture.

"Sample of the same nature" refers to a sample of the same origin withdrawn in substantially the same way in different subjects or in a same subject at different time intervals and, if applicable, having undergone the same treatment step(s).

A "detectable concentration" is a concentration making it possible to detect the presence of a control compound during a test, in particular an immunological test of the sandwich type in which a control compound bonds to a capture antibody fixed on a solid support and is detected by a marked detection antibody.

Preferably, the concentration of a control compound varies little in samples of the same nature.

The expression "the concentration of a control compound varies little in samples of the same nature" here means a concentration that varies by less than 60%, preferably less than 40%, more preferably less than 20% from one sample to another, the concentration being given in µg/mL.

In one advantageous embodiment, a control compound is present in the sample in a concentration of the same order of magnitude as the concentration of the analyte(s) to be detected, when these analytes are present. Preferably, a control compound is present in the sample in a concentration of the same order of magnitude as the concentration of each of the analytes to be detected.

The concentration of a control compound is of the same order of magnitude as the concentration of each of an analyte to be measured.

Preferably, the concentration of the control compound is more than 5 decades lower or higher than that of said analyte to be assayed, when it is present in the sample, preferably at least 4 decades, more preferably at least 3 decades.

For example, the concentration of a control compound is no more than 100 µg/mL, preferably no more than 10 µg/mL, more preferably no more than 1 µg/mL, for a concentration of an analyte to be assayed of 1 ng/mL.

Preferably, the concentration of the control compound is of the same order of magnitude as the concentration of an analyte, when the deviation between the concentration of the analyte in a sample to be analyzed that contains this analyte and that of the control compound is no more than 5 decades, preferably no more than 4 decades, more preferably no more than 3 decades.

In the case of a sample of human or animal origin, a control compound preferably has a structure retained within the human or animal population in question for the analysis. In one preferred embodiment, a control compound has no polymorphism within the considered population.

The control compound preferably is not a marker of a disease.

When at least one analyte is detected by an antibody, a control compound is preferably a compound detectable by an antibody.

The control compound is preferably not altered by any possible prior treatment step(s) of the sample, so as to be detectable by an antibody.

The control compound may be a molecule, or a complex of at least two molecules, which may be identical or different.

As an example, when the sample to be analyzed is a blood or plasma sample, in particular human blood or human plasma, a control compound may be the soluble a coagulation factor, for example a coagulation factor chosen from factors VIII, IX, X, XI, XII or XIII.

In one specific embodiment, a control compound is not factor XIII.

In one particular embodiment, a control compound is not an immunoglobulin of type G (IgG), in particular a human IgG, and/or is not an immunoglobulin of type M (IgM), in particular a human IgM, or more generally, is not an immunoglobulin, in particular a human immunoglobulin.

The soluble receptor of the transferrin complexed to the transferrin is a complex comprising two molecules of the soluble receptor of the transferrin and two transferrin molecules.

For example, the soluble receptor of the transferrin complexed to the transferrin is generally present in a concentration comprised from 0.8 µg/mL to 4 µg/mL in the samples to be analyzed coming from a human subject, independently of the condition of the subject.

When the concentration of a control compound may vary, for example based on the nature of the sample and/or the condition of the subject from which the sample was taken, it may be advantageous to use at least two different control compounds.

Additive

An additive is a compound or a set of compounds that is (are) not present in the sample, i.e., that is (are) not initially present in the sample or that is (are) not derived from a compound initially present in the sample.

An additive may in particular be an antigen or a hapten, said antigen or said hapten being able to be coupled or not coupled to a carrier molecule.

As an example, for a human or animal biological sample, a compound or one of the compounds that is not present in the sample to be analyzed is for example selected from the group consisting of digoxigenin, a plant hormone, an alkaloid, a plant steroid, a nucleic acid and a pesticide.

In one preferred embodiment, the additive is not a nucleic acid.

Digoxigenin is a steroid extracted from certain plants.

A pesticide is for example an insecticide, such as an organophosphate or an organochlorine, and herbicide, such as triazine or phenyl-urea, or combinations thereof.

One preferred additive according to the invention is digoxigenin coupled to a carrier molecule, an auxin coupled to a carrier molecule, a triazine coupled to a carrier molecule, said carrier molecule for example being BSA.

One preferred additive according to the invention is digoxigenin coupled to BSA.

Furthermore, the additive does not interfere with the detection of the analytes during the implementation of a multiplex analysis method. In particular, the additive does not interfere with the analytes to be detected, the capture ligand(s) used, the detection ligand(s) used, the control compound(s), if applicable the reporter(s), if applicable the substrate(s), and the detection of the signal.

In one particular embodiment, the additive does not comprise or consist of biotin or an analogue of biotin and/or avidin or an analogue of avidin (in particular streptavidin or neutravidin), said biotin, avidin or one of their analogues being grafted or not grafted on a carrier molecule.

Capture Ligand

A capture ligand is a compound fixed on a solid support, in particular at a spot or the surface of a bead.

A capture ligand is preferably an antibody or antigen that is fixed on the solid support, in particular at a spot or the surface of a bead.

A capture ligand may be specific to an analyte to be detected in the sample, a control compound or an additive.

A capture ligand may be an antibody, an antigen, a peptide, a carbohydrate, a lipid or a nucleic acid.

In one preferred embodiment, the capture ligand is not a nucleic acid.

In one preferred embodiment, the capture ligand is selected from the group consisting of an antibody, an antigen, a peptide, a carbohydrate and a lipid.

A capture ligand is preferably an antibody or antigen.

When a capture ligand is an antibody, it for example involves a monoclonal antibody or a polyclonal antibody.

Detection Ligand

A detection ligand is intended to reveal the presence of a compound to which it is specific.

A detection ligand may be an antibody, an antigen, a peptide, a carbohydrate, a lipid or a nucleic acid.

In one preferred embodiment, the detection ligand is not a nucleic acid.

In one preferred embodiment, the detection ligand is selected from the group consisting of an antibody, an antigen, a peptide, a carbohydrate and a lipid.

A detection ligand is preferably an antibody or an antigen.

When a detection ligand is an antibody, it for example involves a monoclonal antibody or a polyclonal antibody.

A detection ligand is preferably a marked detection ligand, i.e., a detection ligand to which a detection marker (which may for example be biotin or a peroxidase) is attached, covalently or non-covalently.

When a detection ligand is not marked, its detection may be obtained by using a specific marked antibody of said detection ligand.

A detection ligand may be specific to an analyte to be detected in the sample, a control compound or an additive.

A detection ligand may be identical to the used capture ligand or one of the used capture ligands, with the exception of any presence of a detection marker, and/or bind to the compound to which it is specific at the same zone as that bonded by the capture ligand or one of the capture ligands. In this case, if said capture ligand and said detection ligand are antibodies, it then involves a "homologous sandwich".

A capture ligand and the detection ligand or one of the detection ligands can be specific to separate zones at the compound to which they are specific, so as to avoid competition of the capture ligand and the detection ligand with respect to the compound to which they are specific, due to a steric hindrance. In this case, if said detection ligand and said capture ligand are antibodies, it then involves a "heterologous sandwich".

In one preferred embodiment, a detection ligand and a capture ligand specific to a same compound do not bond to the same location on said compound. More preferably, said detection ligand bonds to a zone of said compound that is far from the binding zone with said capture ligand.

In another preferred embodiment, a detection ligand is identical to a capture ligand, with the exception of any presence of a detection marker, and/or bonds to the compound to which it is specific at the same zone as that bonded by said capture ligand, in particular when the compound to which it is specific is in the form of a complex having at least two identical bonding zones.

Detection Marker

A detection marker may be a direct marker or an indirect marker.

A direct marker is a marker whose signal can be detected directly, i.e., without requiring the prior addition of a reporter.

A direct marker is for example selected from the group consisting of a lanthanide, a luminescent compound, a transition metal such as ruthenium, a chromogenic, and colored, fluorescent or luminescent nanoparticles.

In the present application, a "luminescent compound" in particular designates an electroluminescent, thermoluminescence or (preferably) chemiluminescent compound.

One example luminescent compound (more specifically, thermoluminescent compound) that may be used as a direct marker consists of silica nanoparticles comprising (for example doped with) molecules of a dioxetane compound, in particular the 1,2-dioxetane compound, or a derivative of a dioxetane compound, for example a derivative of 1,2-dioxetane.

An indirect marker is a marker for which detection of the signal requires the prior addition of a reporter, and if applicable, the addition of a substrate of the marker coupled to said reporter.

A reporter is a substrate of the indirect marker or a molecule specifically bonding to the indirect marker, said molecule itself being a direct or indirect marker or itself being coupled to a direct or indirect marker.

An indirect marker may for example be an enzyme (in particular, an enzyme producing a luminescent compound from a substrate), biotin, avidin, streptavidin, neutravidin, a hapten, an antigen or an antibody.

A reporter of an enzyme is for example a substrate of said enzyme.

A reporter of a luminescent compound is for example an enzyme or a catalyst.

A reporter of the biotin is, for example, avidin, streptavidin or neutravidin, preferably coupled with a direct marker or an indirect marker, such as an enzyme or a catalyst.

An example enzyme is peroxidase, for example horseradish peroxidase (HRP).

One preferred biotin reporter according to the invention is streptavidin coupled with a peroxidase, preferably horseradish peroxidase.

In one particular embodiment of the invention, the detection marker or one of the detection markers used is or has as substrate, luminol (3-aminophthalhydrazide, also called 5-amino-2,3-dihydro-phthalazine-1,4-dione, molecular formula $C_8H_7N_3O_2$), isoluminol (also called 4-aminophthalhydrazide), an acridine, coelenterazine, dioxetane or peroxyoxalic compound, or one of their derivatives, and in particular a compound described in the publication Dodeigne C. et al (2000), *Talanta* 51, 415-439, "Chemiluminescence as diagnostic tool. A review".

According to one preferred embodiment of the invention, the detection marker or one of the detection markers used has, as substrate, luminol, isoluminol, or one of their derivatives.

A derivative of luminol or isoluminol is preferably a molecule obtained from the luminol or the isoluminol, respectively, through all possible modification(s) (for example, chemical and/or enzymatic). A derivative of luminol or isoluminol is for example a substrate of a peroxidase enzyme, the reaction of said peroxidase enzyme with said derivative of the luminol or the isoluminol making it possible to produce a chemiluminescent compound.

A derivative of the isoluminol may for example be aminoethylisoluminol (or AEI), aminoethylethylisoluminol (or AEEI), aminobutylisoluminol (or ABI), aminobutylethylisoluminol (or ABEI), aminopentylethylisoluminol (or APED, aminohexylisoluminol (or AHI), aminohexylethylisoluminol (or AHEI), aminooctylmethylisoluminol (or AOMI) or aminooctylethylisoluminol (or AOEI), as described in the publication Dodeigne C. et al (2000), *Talanta* 51, 415-439, "Chemiluminescence as diagnostic tool. A review".

Developing

The developing step(s) correspond(s) to the detection of the signal produced by the detection marker(s).

When the detected signal is a fluorescence luminescence signal, the "produced signal" is in particular an "emitted signal".

The developing step(s) depend(s) on the type of marker used.

The signal produced or emitted by a direct marker of the fluorophore type can be read directly by fluorescence.

An indirect marker of the enzyme type, the luminescent compound type or the biotin type requires the addition of a reporter.

As indicated above, an indirect marker of the biotin type requires the addition of a reporter, preferably a reporter coupled to a marker.

If a reporter is coupled to an indirect marker, for example an enzyme, it is necessary to add, in a later step, a substrate of that indirect marker, for example a substrate of that enzyme.

As an example, if a reporter is coupled to the peroxidase, it is necessary to add, in a later step, a substrate of that enzyme, such as luminol.

In one preferred embodiment, a signal detected by chemiluminescence, said signal being produced by a chemiluminescent compound produced by the reaction of a peroxidase enzyme with its substrate, for example luminol, isoluminol and/or a derivative generally also requires the presence of an oxidizer and, if applicable, an electron mediator.

Generally, the chemiluminescence reaction is done using a kit comprising at least two solutions.

The first solution comprises the substrate for the peroxidase, for example the luminol, the isoluminol and/or a derivative of the luminol or the isoluminol, and an electron mediator; the second solution comprises an oxidizer. As an example, it is possible to use the following kits: "Immun-star western C" (Bio-Rad, United States), "ELISTAR ETA C Ultra ELISA" (Cyanagen, Italy), "Supersignal West Pico" (Thermo Scientific, United States), "Chemiluminescent Sensitive Plus HRP" (Surmodics, United States).

Solid Support Appropriate for a Secure Multiplex Analysis

The support(s) used to carry out the analysis method according to the invention are solid supports.

A solid support can be made from any material appropriate to carry out the analysis method.

A solid support is for example a support with a base of a polymer or a mixture of polymers. An appropriate solid support according to the invention is for example a support made from polystyrene, polypropylene, poly(meth)acrylate, polybutadiene or combinations thereof.

Another type of appropriate solid support according to the invention is for example an inorganic support, such as glass, and/or a metal support.

A support may be in the form of a plate, a microplate, a slide, beads or a membrane.

Another example of an appropriate solid support is a membrane, for example a membrane made from nitrocellulose, PVDF (polyvinylidene fluoride), nylon or combinations thereof.

One preferred solid support is made from polystyrene or polypropylene.

Depending on the technology used, the multiplex analysis method can be carried out using a single solid support, for example a solid support comprising at least one compartment, said compartment comprising at least two spots, or on a set of solid supports, for example a set of beads.

The controls according to the invention are transposable to use on a single solid means of the analytes are in the form of spots, and in the second case, the controls and the detection means of the analytes are in the form of beads.

The beads (which may also be called "particles", "microbeads" or "microparticles") can be in solution or suspension or fixed on another solid support, for example a plate, a microplate, a slide or a membrane, and in particular fixed to the bottom of one or several wells of a solid support (for example of a microplate).

Depending on the solid support(s) used, a control of the deposition of a sample is called spot to control the deposition of a sample or bead to control the deposition of a sample; a control of the deposition of one or several detection ligand(s) of an analyte is called spot to control the deposition of a detection ligand of an analyte or bead to control the deposition of a detection ligand of an analyte; and a control of the deposition of a reporter is called spot to control the deposition of a reporter or bead to control the deposition of a reporter.

In one preferred embodiment, the solid support(s) are appropriate for implementing a multiplex analysis in the form of an immunological test of the sandwich type.

A solid support according to the invention also has the advantage of being able to detect analytes independently from the matrix of the sample. For example, the detection of analytes present in the blood may be carried out using a solid support according to the invention from a blood sample or a blood derivative, such as plasma or serum, or a mixture of blood and/or blood derivative samples.

Solid Support Appropriate for a Secure Multiplex Analysis on Spots

The present invention particularly relates to a solid support appropriate for a multiplex analysis of at least one sample, comprising at least one compartment, said compartment comprising at least one control spot and at least two detection spots for an analyte, characterized in that said control spot is selected from the group consisting of a spot for controlling the deposition of a sample, a spot for controlling the deposition of a detection ligand of an analyte and a spot for controlling the deposition of a reporter.

A solid support comprises at least one compartment (also called analysis zone), preferably at least two compartments.

According to one particular embodiment of the invention, a solid support comprises a single compartment. Said single compartment may be a compartment comprising one or several walls. Alternatively, said single compartment can have no walls and then be comparable to the solid support itself. The bottom of the compartment can then consist of single compartment that may or may not include one or several walls is a slide or a membrane.

In one particular embodiment of the invention where a solid support (for example a slide or a membrane) comprises a single compartment, typically, at least one (for example one or two) solid support is used per sample to be analyzed.

When a solid support comprises at least two compartments, they are isolated from one another, such that they do not communicate with one another, i.e., such that the various compositions or solutions used for the analysis cannot circulate from one compartment to another during the analysis. Thus, a solution added into one compartment will not go into the other compartments. For example, the compartment(s) comprise or are made up of a bottom and one or several walls, said wall(s) isolating the compartment(s) from one another such that they do not communicate with one another.

One compartment of the solid support is used per sample to be analyzed.

One example compartment is a well.

A solid support is for example a microplate.

The microplate is typically a microplate with 96 wells or 384 wells.

A compartment of the solid support used to analyze a sample comprises at least three spots, for example three spots, four spots or five spots, or at least six spots, preferably six spots, seven spots, eight spots, more preferably at least nine spots, for example nine spots, ten spots, eleven spots, twelve spots, thirteen spots, fourteen spots, fifteen spots, sixteen spots or more than sixteen spots.

Here, a "spot" refers to a zone of a compartment of a solid support comprising at least one compound of interest bonded to the surface of said compartment, through noncovalent physicochemical interactions (in particular of the weak bond type, for example, ionic, van der Waals, hydrogen and/or hydrophobic) and/or by covalent bonds.

A spot may comprise, aside from the compound(s) of interest, at least one polymer, in particular at least one polymer including hydrophilic groups, for example at least one hydrogel.

"At least", within the meaning of the present application, refers to one or several, several in particular meaning two, three, four, five, six, seven, eight, nine, ten, eleven, twelve, thirteen, fourteen, sixteen or more than sixteen.

A spot corresponds to a well-defined zone, generally spherical or oval and small, for example comprised between $0.0078$ $mm^2$ to $5.309$ $mm^2$, preferably from $0.196$ $mm^2$ to $3.142$ $mm^2$, more preferably comprised from $0.503$ $mm^2$ to $2.011$ $mm^2$.

A spot may have a discoid, cylindrical or approximately discoid or cylindrical shape, for example oval, in particular when a solid support is a microplate or a slide.

Alternatively, a spot may have a square or rectangular shape (this may in particular be a strip), for example when a solid support is a membrane, or any other shape.

The spots are obtained using techniques well known by those skilled in the art, such as those disclosed in U.S. Pat. No. 7,470,547 B2, U.S. Pat. Nos. 6,576,295 B2, 5,916,524 A and 5,743,960 A.

For example, a spot is obtained by depositing at least one drop of a solution containing a determined quantity of said compound(s) of interest in a specific location on the surface of the compartment.

When a spot comprises at least one polymer (for example at least one hydrogel), said spot may be obtained by depositing at least one drop of a solution containing a determined quantity of said compound(s) of interest in a specific location on the surface of the compartment on which said polymer has been previously deposited.

A spot can also be obtained by in situ synthesis of said compound(s) of interest in a specific location on the surface of the compartment. Said compound(s) of interest are qualified as probes in this case. This may involve a nucleic acid or a peptide (see for example document U.S. Pat. No. 5,143,854).

The surface of the compartment is also called "solid phase".

A compound of interest is generally a capture ligand, a carrier molecule coupled to an indirect marker or an indirect marker. The capture ligand, the carrier molecule coupled to an indirect marker and the indirect marker are in particular as defined above.

In one advantageous embodiment, each compartment of a solid support comprises the same number of spots. Furthermore, each compartment of a solid support comprises the same number of spots and the same spot composition.

In another advantageous embodiment, a support may comprise one or several compartments without spots, or with a different number of spots and/or spot composition. Part or all of a support may for example comprise at least two separate groups (or types) of spots or compartments, each of the separate groups having a different number of spots and/or spot composition.

A compartment comprises at least one control spot (for example, at least one spot for controlling the deposition of a sample), preferably at least two control spots, and at least two detection spots for an analyte.

A compartment generally comprises at least one spot per analyte to be detected, each analyte for example being able to correspond to an infection or disease to be detected, the evolution of an infection or disease, a condition (pathological or not) of the subject, a risk of developing a condition (pathological or not) or a marker of resistance to a treatment. Several spots of a compartment may also be intended to analyze a same analyte.

The spot for controlling the deposition of a sample or for controlling the deposition of a detection ligand of an analyte preferably comprises a capture ligand. The capture ligand is in particular as defined above.

A same spot may comprise several different capture ligands (for example, several antibodies and/or antigens), which are generally specific to a same pathology, infection or disease to be detected (in particular specific to a same virus, a same bacteria, a same fungus or a same parasite), or specific to a same evolution of an infection or disease, a same condition (pathological or not) of a subject, a same risk of developing a condition (pathological or not) or a same marker of resistance to a treatment.

The present invention particularly relates to a solid support appropriate for a multiplex analysis of at least one sample, comprising at least one compartment, said compartment comprising at least one control spot and at least two detection spots for an analyte, characterized in that said control spot is a spot for controlling the deposition of a sample or a spot for controlling the deposition of a detection ligand of an analyte. Said compartment may further comprise at least one spot for controlling the deposition of a reporter.

In one preferred embodiment, the spot for controlling the deposition of a sample or for controlling the deposition of a detection ligand of an analyte comprises one or at least one capture ligand, said capture ligand(s) not being a nucleic acid.

More generally, the spot for controlling the deposition of a sample or for controlling the deposition of a detection ligand of an analyte preferably does not comprise nucleic acid.

In one preferred embodiment, the spot for controlling the deposition of a sample or for controlling the deposition of a detection ligand of an analyte comprises one or at least one capture ligand selected from the group consisting of an antibody, an antigen, a peptide, a carbohydrate and a lipid.

The present invention particularly relates to a solid support appropriate for a multiplex analysis of at least one sample, comprising at least one compartment, said compartment comprising at least two control spots and at least two detection spots for an analyte, characterized in that said control spots are selected from the group consisting of a spot for controlling the deposition of a sample, a spot for controlling the deposition of a detection ligand of an analyte and a spot for controlling the deposition of a reporter.

A solid support according to the invention allows a secure multiplex analysis.

In one advantageous embodiment, the present invention relates to a solid support appropriate for a multiplex analysis of at least one sample, comprising at least one compartment, said compartment comprising at least two control spots and at least two detection spots for an analyte, characterized in that said control spots are selected from among a spot for controlling the deposition of a sample and a spot for controlling the deposition of a detection ligand of an analyte.

The compartment(s) of the solid support may for example comprise at least two spots for controlling the deposition of a sample or at least two spots for controlling the deposition of a detection ligand of an analyte.

In one preferred embodiment, the compartment(s) of the solid support comprise at least one spot for controlling the deposition of a sample and at least one spot for controlling the deposition of a detection ligand of an analyte.

As explained above, in case of indirect marking of at least one detection ligand, it is useful for the compartment(s) to comprise at least one spot for controlling the deposition of a reporter.

The present invention also relates to a solid support appropriate for a multiplex analysis of at least one sample, comprising at least one compartment, said compartment comprising at least one spot for controlling the deposition of a sample, at least one spot for controlling the deposition of a detection ligand of an analyte, at least one spot for controlling the deposition of a reporter, and at least two spots for detecting an analyte.

The compartment(s) of the solid support may therefore comprise at least two spots for controlling the deposition of a reporter, for example two or three spots for controlling the deposition of a reporter, for analyses involving at least two different indirect markers. In such a case, each spot for controlling the deposition of a reporter is specific to a marker.

Set of Beads Appropriate for a Secure Multiplex Analysis

When a solid support is a bead, the multiplex analysis method for a sample is done with a set of beads.

The present invention thus also relates to a set of beads appropriate for a multiplex analysis of a sample, comprising at least one control bead and at least two detection beads for an analyte, characterized in that the control bead is selected from the group consisting of a bead for controlling the deposition of a sample, a bead for controlling the deposition of a detection ligand of an analyte and a bead for controlling the deposition of a reporter.

Within the meaning of the present application, "at least one bead X" means at least one type (or group) of beads X, "bead X" being able to mean "control bead", "bead for controlling the deposition of a sample", "bead for controlling the deposition of a detection ligand of an analyte" or "bead for controlling the deposition of a reporter".

A "type of beads" (or "group of beads") within the meaning of the invention comprises or consists of several beads (for example 10, 50, 100, 200, 300 or 500 beads), which are identical to one another or at least several beads on the surface of which the same compound(s) of interest is (are) fixed.

Similarly, "at least two beads X" respectively means at least two beads X or two different types (or "groups") of beads X, "bead X" being able to mean "control bead", "bead for detecting an analyte", "bead for controlling the deposition of a sample", "bead for controlling the deposition of a detection ligand of an analyte" or "bead for controlling the deposition of a reporter".

Each bead is also covered with at least one compound of interest bonded to the surface of the bead, also called "solid phase".

A set of beads used to analyze a sample comprises at least three beads (or types of beads), for example three, four or five beads (or types of beads), or at least six beads (or types of beads), preferably six, seven, eight beads (or types of beads), more preferably at least nine beads (or types of beads), for example nine, ten, eleven, twelve, thirteen, fourteen, fifteen beads or sixteen beads (or types of beads), or more than sixteen beads (or types of beads).

In the present application, "bead", "particle", "microbead" or "microparticle" means any particle, preferably spherical or approximately spherical, with a size that may be comprised from 0.3 µm to 100 µm in diameter, preferably from 0.5 µm to 40 µm. Such particles are for example manufactured by the companies Luminex, Merck and Dynal. A bead able to be used in the context of the present invention may also be a particle in the form of a cube or slab or approximately in the form of a cube or slab, the length of the sides of which would for example be comprised from 0.3 µm to 100 µm, preferably from 0.5 µm to 40 µm.

A bead according to the invention is preferably made up of one or several polymers that are inert relative to the components of the biological samples; it is solid and insoluble in the samples to be analyzed. Examples of inert polymers that may be used are a polyester, polyether, polyolefin, polyamide, polysaccharide, polyurethane or cellulose.

One or several functional groups may be incorporated with said inert polymer(s) to allow the fixing or coupling of one or several compounds of interest (for example proteins, peptides, glycoproteins, lipids, carbohydrates or nucleic acids). These functional groups, known by those skilled in the art, may be selected from the group consisting of amine (=NH2) functions or ammonium functions (—NH3+ or —NHR, R representing an aliphatic chain, preferably an:
 alkyl chain from 1 to z carbon atoms, linear or branched (substituted or not), z preferably being an integer comprised from 1 to 20,
 alkenyl chain from 2 to z carbon atoms, linear or branched, z preferably being an integer comprised from 1 to 20, or
 an aryl radical),
alcoholic functions (—OH), carboxylic functions (—COOH), isocyanate functions (—NCO), thiol functions (SH) or epoxy functions. The most commonly used monomers to introduce —COOH carboxylic functions into the polyolefins are acrylic acid or methacrylic acid.

A bead is in fact covered with one or several compounds of interest, using any appropriate method well known by those skilled in the art. The fixing of the compound(s) of interest on the surface of a bead may be done by electrostatic attraction, affinity interaction, hydrophobic interaction and/or covalent coupling.

In one preferred embodiment, the compound(s) of interest are fixed to the surface of the bead by covalent coupling.

The methods for fixing one or several compounds to the surface of a bead are well known by those skilled in the art (cf. for example LUMINEX xMAP® Antibody Coupling KitUser Manual, the article by Joseph Dasso et al. (*Journal of Immunological Methods* 263 (2002) 23-33) or document WO1997/014028).

For example, in the case of the bead comprising carboxyl chemical functions on its surface, these chemical functions may be converted into an activated ester formed by a reaction with the 1-ethyl-3-(3-dimethylaminopropyl)carbodiimide hydrochloride and N-hydroxysulfosuccinimide. A compound of interest, such as an antibody, a protein or a peptide, may then be grafted, by a free amine group present on said compound of interest, on the activated ester groups of each bead. The conversion into an activated ester form and the coupling of the compound of interest on a bead are done using procedures well known by those skilled in the art (cf. for example U.S. Pat. No. 7,141,362).

The beads or part of the beads of a set of beads are preferably magnetic beads, such as beads using the Luminex xMAP® technology, in order to allow the recovery of the beads between the different steps of the method, and in particular at the end of the washing steps.

Each bead is marked with a code so as to be able to differentiate it from the other beads of the set of beads, for example a fluorescence code or a barcode.

The marking of a bead with a code, for example by fluorescence or a barcode, can be done using any appropriate method well known by those skilled in the art, for example as described in documents EP 1,802,710 and EP 1,049,807.

As for a solid support comprising at least one compartment, a compound of interest is generally a capture ligand, a carrier molecule coupled to an indirect marker or an indirect marker. The capture ligand, the carrier molecule coupled to an indirect marker and the indirect marker are in particular as defined above.

The set of beads according to the invention comprises one bead (or type of beads) per desired control and at least one bead (or at least one type of beads) per analyte to be detected. Several beads (or types of beads) can also be intended to detect a same analyte.

The bead for controlling the deposition of a sample or for controlling the deposition of a detection ligand of an analyte preferably comprises a capture ligand. The capture ligand is in particular as defined above.

A same bead (or each bead of a given type of beads) may be covered with several different capture ligands (for example, several antibodies and/or antigens), which are generally specific to a same infection to be detected, and in particular specific to a same virus, a same bacteria or a same parasite.

The set of beads therefore comprises at least one control bead (for example, at least one bead for controlling the deposition of a sample), preferably at least two control beads, and at least two detection beads for an analyte.

At least one set of beads is used per sample to be analyzed.

The present invention particularly relates to a set of beads appropriate for a multiplex analysis of at least one sample, comprising at least one control bead and at least two detection beads for an analyte, characterized in that said control bead is a bead for controlling the deposition of a sample or a bead for controlling the deposition of a detection ligand of an analyte. Said set of beads may further comprise at least one bead for controlling the deposition of a reporter.

In one preferred embodiment, the bead for controlling the deposition of a sample or for controlling the deposition of a detection ligand of an analyte comprises one or at least one capture ligand, said capture ligand(s) not being a nucleic acid.

More generally, the bead for controlling the deposition of a sample or for controlling the deposition of a detection ligand of an analyte preferably does not comprise nucleic acid.

In one preferred embodiment, the bead for controlling the deposition of a sample or for controlling the deposition of a detection ligand of an analyte comprises one or at least one capture ligand selected from the group consisting of an antibody, an antigen, a peptide, a carbohydrate and a lipid.

The present invention particularly relates to a set of beads appropriate for a multiplex analysis of a sample, comprising at least two control beads and at least two detection beads for an analyte, characterized in that said control beads are selected from the group consisting of a bead for controlling the deposition of a sample, a bead for controlling the deposition of a detection ligand of an analyte and a bead for controlling the deposition of a reporter.

In one advantageous embodiment, the present invention relates to a set of beads appropriate for a multiplex analysis of a sample, comprising at least two control beads and at least two detection beads for an analyte, characterized in that said control beads are chosen from among a bead for controlling the deposition of a sample and a bead for controlling the deposition of a detection ligand of an analyte.

The set of beads may for example comprise at least two beads for controlling the deposition of a sample or at least two beads for controlling the deposition of a detection ligand of an analyte.

In one preferred embodiment, the set of beads comprises at least one bead for controlling the deposition of a sample and at least one bead for controlling the deposition of a detection ligand of an analyte.

As explained above, in case of indirect marking of at least one detection ligand for an analyte, it is advantageous to use at least one bead for controlling the deposition of a reporter.

The present invention also relates to a set of beads appropriate for a multiplex analysis of a sample, comprising at least one bead for controlling the deposition of a sample, at least one bead for controlling the deposition of a detection ligand of an analyte, at least one bead for controlling the deposition of a reporter and at least two beads for detecting an analyte.

The set of beads may therefore comprise at least two beads for controlling the deposition of a reporter, for example two or three beads for controlling the deposition of a reporter, for analyses involving at least two different indirect markers. In such a case, each bead for controlling the deposition of a reporter is preferably specific to a marker.

The set of beads according to the invention allows a secure multiplex analysis.

Control of the Deposition of a Sample

The control of the deposition of the sample makes it possible to verify that the sample has been placed in the presence of the spots of a compartment of the solid support or with a set of beads.

The control of the deposition of a sample comprises at least one capture ligand, in particular an antibody or an antigen, specific to a control compound naturally present in the sample to be analyzed. The control compound is in particular as defined above.

Thus, a signal detected at the control of the deposition of a sample makes it possible to validate the deposition step of the sample.

The deposition of a sample consists of adding a sample to be analyzed into a compartment of the solid support according to the invention comprising at least one control spot and at least two analyte detection spots, or placing the sample in the presence of at least one set of beads according to the invention.

A control compound then fixes to the capture ligand at the sample deposition control. A control compound thus fixed can be detected by a specific detection ligand of the control compound.

Preferably, a detection ligand of a control compound is specific to a zone of the control compound remote from the zone of the control compound to which the capture ligand used specifically bonds, so as to avoid competition of the capture ligand and the detection ligand with respect to the control compound, due to a steric hindrance.

When a control compound is a complex of at least two molecules, the detection ligand or one of the detection ligands can be specific to one of the two molecules and the capture ligand or one of the capture ligands can be specific to the other molecule of the complex.

Alternatively, when a control compound is a complex of at least two molecules, the detection ligand or one of the detection ligands and the capture ligand or one of the capture ligands can be specific to the same molecule, and even the same zone of the molecule, when the complex comprises at least two of these identical molecules, thereby allowing the simultaneous fixing of the detection antibody and the capture antibody on the complex.

For example, when a control compound is the soluble receptor of the transferrin complexed to the transferrin, a deposition control may comprise, as capture ligand, a specific antibody either of the transferrin, or of the soluble receptor of the transferrin. Preferably, the or one of the capture ligand(s) is a specific antibody of the soluble receptor of the transferrin, in order to avoid interference with the free transferrin that may be found in a blood sample.

In one preferred embodiment, the or one of the capture ligand(s) of the deposition control is specific to the soluble receptor of the transferrin and the or one of the detection ligand(s) of the or a control compound is either specific to the transferrin, or specific to the soluble receptor of the transferrin.

In certain embodiments, a control of the deposition of a sample also makes it possible to verify that one or several analyte detection ligand(s) have been placed in the presence of the spots of a compartment of a solid support or of a set of beads, when said analyte detection ligand(s) are not added at the same time as sample to be analyzed, but for example in a later step, at the same time as the addition of the detection ligand(s) of the control compound. "At the same time as the addition of the detection ligand(s) of the control compound" generally means that said analyte detection ligand(s) are added in the form of a solution comprising said analyte detection ligand(s) and the detection ligand(s) of the control compound.

Alternatively, said analyte detection ligand(s) and said detection ligand(s) of the control compound can be added in the same step, but in the form of separate solutions.

Indeed, when a sample to be analyzed comprises a compound that could interfere with the detection ligand of the control compound, it may be necessary to add the detection ligand to the control compound in a step after the deposition step of the sample, in particular after the deposition step of the sample followed by at least one washing step. In this case, all or part of the detection ligand(s) of the analytes can be added at the same time as the detection ligand of the control compound. The control of the deposition then also makes it possible to validate that these detection ligands have been placed in the presence of the spots of a compartment of the solid support or of the set of beads.

For example, a blood sample comprises both the soluble receptor of the transferrin complexed to the transferrin and the free transferrin, i.e., not bonded to the receptor. Thus, if the or one of the detection ligand(s) is a specific antibody of the transferrin and it is added at the same time as the sample, it would risk bonding in part to the free transferrin, and the detection of the control compound would be distorted. In such a case, said detection ligand of the control compound is contributed in a subsequent step, i.e., after the deposition step of the sample followed by at least one washing step.

In one particular embodiment, the control(s) of the deposition of the sample do not comprise a specific antibody of factor XIII (i.e., neither a specific antibody of the tetrameric form, nor a specific antibody of a subunit of factor XIII). Preferably, the control(s) of the deposition of a sample do not comprise a specific capture ligand of factor XIII (i.e., neither a specific capture ligand of the tetrameric form, nor a specific capture ligand of a subunit of factor XIII).

In one particular embodiment, the control(s) of the deposition of a sample do not comprise a specific capture ligand (in particular a specific antibody) of an IgG, an IgM or more generally an immunoglobulin (in particular a human IgG, a human IgM or a human immunoglobulin).

It may be very advantageous to use at least two controls of the deposition of a sample, these controls detecting different control compounds and/or a same control compound but with different sensitivities, for example when the concentration of the control compound may vary, for example based on the nature of the sample and/or the condition of the subject from which the sample was taken, it may be advantageous to use at least two different control compounds.

Control of the Deposition of a Detection Ligand of an Analyte

The control of the deposition of a detection ligand of an analyte makes it possible to verify that one or several analyte detection ligand(s) deposited at the same time as the detection ligand of an additive and/or one or several analyte detection ligand(s) deposited at the same time as an additive have been placed in the presence of the spots of a compartment of a solid support or of a set of beads.

"Deposited at the same time as the detection ligand of an additive" generally means that said analyte detection ligand(s) are added in the form of a solution comprising said analyte detection ligand(s) and the detection ligand(s) of an additive. Alternatively, said analyte detection ligand(s) and/or the detection ligand(s) of an additive can be added in the same step, but in the form of separate solutions.

"Deposited at the same time as an additive" generally means that said analyte detection ligand(s) are added in the form of a solution comprising said analyte detection ligand(s) and an additive. Alternatively, said analyte detection ligand(s) and/or one or several additives can be added in the same step, but in the form of separate solutions.

The control of the deposition of a detection ligand of an analyte also makes it possible to verify the incubation and washing steps. Indeed, the concentration of the additive placed in the presence of the spots of a compartment of the solid support or of a set of beads being known, a variation of the detected signal makes it possible to identify a deficiency of the method at the steps of the method, and in particular the incubation and washing steps. This may in particular made it possible to avoid "false positives" resulting from deficient incubation and/or washing steps, i.e., not done or done poorly.

A "false positive" is a positive result reflecting the presence of one or several analytes to be detected in a sample, whereas said analyte(s) were not present in the sample and therefore should not have been detected.

The control of the deposition of a detection ligand of an analyte comprises at least one specific capture ligand of an additive that is not present in the sample to be analyzed and that is used during the implementation of the multiplex analysis method. An additive is in particular as defined above.

Thus, a signal detected at the control of the deposition of a detection ligand of an analyte makes it possible to validate the deposition step of the analyte detection ligand(s) deposited at the same time as the detection ligand of an additive.

An additive placed in the presence of the spots and/or of a set of beads fixes to the capture ligand at the control of the deposition of a detection ligand of an analyte. An additive thus fixed can be detected by a specific detection ligand of said additive.

For example, when an additive comprises digoxigenin, a capture ligand of the method control may be a specific antibody of the digoxigenin. Preferably, a detection ligand of an additive is also a specific antibody of digoxigenin.

It may be advantageous to use several different controls of the deposition of a detection analyte, and therefore an equal number of different additives, for example if the detection ligands of the analytes are added in several different steps, in particular during at least three different steps.

According to one particular embodiment of the invention,
a control compound that fixes to a capture ligand of a deposition control of the sample during the implementation of the analysis method according to the invention is detected by a specific detection ligand of said control compound (immunological format of the sandwich type), and
an additive that fixes to a capture ligand of a deposition control of a detection ligand of an analyte during the implementation of the analysis method is detected by a specific detection ligand of said additive (immunological format of the sandwich type).

These sandwich-type immunological formats make it possible to achieve a high level of specificity and/or sensitivity, compared to other immunological formats, and in particular indirect formats.

Control of the Deposition of a Reporter

The control of the deposition of a reporter makes it possible to verify that the detection marker reporter has been placed in the presence of the spots of a compartment of a solid support or of a set of beads.

The control of the deposition of a reporter is only useful in case of indirect marking of at least one detection ligand of an analyte.

The control of the deposition of a reporter comprises an indirect marker or a carrier molecule coupled to an indirect marker.

The indirect marker of the control of the deposition of a reporter is identical to the indirect marker of at least one detection ligand of an analyte.

If at least two different indirect markers are used to detect at least two analyte detection ligands, it is preferable to use a control of the deposition of a reporter for each marker.

In one advantageous embodiment according to the invention, a single and same indirect marker is used to mark the detection ligand(s), and therefore a single control of the deposition of a reporter can be used.

Thus, a signal detected at the control of the deposition of a reporter makes it possible to validate the deposition step of the reporter of the corresponding detection marker.

The reporter thus fixes to the detection marker at the control of the deposition of a reporter and a signal is obtained, if necessary after adding the substrate of the marker of said reporter, in case of positive control of the deposition of a reporter.

For example, when the indirect marker is biotin, the control of the deposition of a reporter comprises biotin or a carrier molecule coupled to biotin.

Secure Multiplex Analysis Method

The present invention thus relates to a multiplex analysis method for detecting at least n analytes in at least one sample, n being an integer greater than or equal to 2, said method comprising at least steps a), c) and e), at least steps a), c) and f) or at least steps a), b), c) and d) as follows:
 a) providing at least one solid support comprising at least one compartment as defined above or at least one set of beads as defined above,
 b) placing, in the presence of the spots of said compartment or said set of beads: l detection ligands of p analytes to be detected, and, if applicable, at least one additive, l preferably being greater than or equal to p,
 c) placing a sample to be analyzed in the presence of the spot(s) of said compartment or of said set of beads,
 d) placing, in the presence of the spots of said compartment or of said set of beads:
   l' detection ligands of m analytes to be detected, and, if applicable, at least one detection ligand of said additive(s), l' preferably being greater than or equal to m,
 e) placing, in the presence of the spots of said compartment or of said set of beads:
   at least one detection ligand of a control compound and l'' detection ligands of y analytes to be detected, l'' preferably being greater than or equal to y, and
 f) optionally placing at least one reporter in the presence of the spots of said compartment or of said set of beads,
 g) optionally, in particular when said or one of said reporters of step f is coupled to a marker, in particular an indirect marker (for example, an enzyme), placing at least one second reporter of said marker coupled to the reporter of step f) (for example, a substrate, such as luminol, isoluminol or one of their derivatives) in the presence of the spots of said compartment or said set of beads,
 l, l', l'', m, p and y being integers greater than or equal to 0 and the sum m+p+y being greater than or equal to 1.

A method for detecting at least n analytes may consist of detecting a different number of analytes that is less than n, when at least two analytes to be detected are identical. For example, at least two spots of a compartment of a solid support or at least two beads (or types of beads) of a set of beads are intended to detect a same analyte.

The number "n" is generally equal to the number of detection spots of an analyte of a compartment of a solid support or the number of beads (or types of beads) for detecting an analyte of a set of beads.

Preferably, the sum m+p+y is comprised from 1 to n.

When several analytes to be detected are identical, it is possible to use a same detection ligand for at least two or all of the identical analytes. The sum m+p+y may then be greater than or equal to 1 and strictly less than n.

In another embodiment, the sum m+p+y is equal to n, for example when there are n detection spots of an analyte in a compartment of a solid support or n beads (or types of beads) for detecting an analyte of a set of beads.

As outlined below, steps a) to e) can be done simultaneously and/or successively (for example, some of these steps may be done simultaneously, while others are done successively), at least for two of them in the order a) to e) or in another order, step a) always being the first step carried out; when the method [comprises] step f) and optionally step g), these steps are always carried out after steps a) to e).

When the method comprises at least steps a), c) and e), a solid support comprises at least one compartment, said compartment comprising at least one spot for controlling the deposition of a sample, or a set of beads comprises at least one bead for controlling the deposition of a sample.

When the method comprises at least steps a), c) and f), a solid support comprises at least one compartment, said compartment comprising at least one spot for controlling the deposition of a reporter, or a set of beads comprises at least one bead for controlling the deposition of a reporter.

When step b) comprises placing the spots or the set of beads in the presence of at least one additive, step d) preferably comprises placing the spots or the set of beads in the presence of at least one detection ligand of said additive(s).

When the method comprises at least steps a), b), c) and d), at least one additive being placed in the presence of the spots or of the set of beads in step b) and at least one detection ligand of said additive(s) being placed in the presence of the spots or the set of beads in step d), a solid support comprises at least one compartment, said compartment comprising at least one spot for controlling the deposition of a detection ligand of an analyte, or a set of beads comprises at least one bead for controlling the deposition of a detection ligand of an analyte.

When the method comprises steps a), b), c) and d), but does not comprise step e), at least one additive is placed in the presence of the spots or of the set of beads in step b) and at least one detection ligand of said additive(s) is placed in the presence of the spots or the set of beads in step d).

The expression "place a compound X in the presence of the spots of a compartment" means that the compound X is added into a compartment comprising said spots, said compartment being intended to analyze a sample.

The expression "place a compound X in the presence of a set of beads" means that the compound X is placed in the presence of at least one set of beads intended to analyze a sample in any appropriate container containing said set of beads. One example of an appropriate container is a microtube, a microplate or a reaction dish.

When at least two of steps b) to f) are done simultaneously, the compound(s) X may be placed separately in the presence of the spot(s) of a compartment or of the bead(s) or of the set(s) of beads intended to analyze a sample, i.e., in the form of separate compositions. Alternatively, these compounds X or some of these compound(s) X may be placed in the presence of the spot(s) of a compartment or of the bead(s) or of the set(s) of beads intended to analyze a sample in the form of one or several mixtures.

The different compounds are placed in the presence of spots of each compartment or each set of beads for a certain length of time, for example from 1 second to 2 hours, preferably 1 minute to 1 hour, more preferably 5 minutes to 50 minutes, still more preferably from 10 minutes to 40 minutes.

One skilled in the art knows how to determine the appropriate temperature for each incubation step. The temperature of an incubation may for example be 4° C., a temperature comprised from 19° C. to 24° C., 37° C. or 40° C.

The different components used during steps b), d), e), f) and g) are well known by those skilled in the art. They for example make it possible to form antigen-antibody, marker-reporter complexes.

Step a) consists of providing a solid support as defined above comprising at least one compartment or at least one set of beads as defined above.

Step a) in particular means that the multiplex analysis method is implemented using said solid support or said set of beads, i.e., using said solid support or said set of beads.

The multiplex analysis method according to the invention is therefore implemented either by using a solid support with compartment(s), for example of the microplate type, or with a set of beads.

For x samples to be analyzed, step a) consists of providing:
- a solid support comprising at least x compartments or several solid supports so as to have at least x compartments with all of the solid supports (for example, when a solid support includes only one compartment, which may, in one particular embodiment, be likened to the solid support itself, providing at least x solid supports), or
- at least x sets of beads.

The multiplex analysis method according to the invention for example makes it possible to detect n analytes in at least 1 sample, at least two samples, at least 5 samples, at least 10 samples, preferably at least 20 samples, for example at least 40 samples, at least 60 samples or at least 80 samples.

The number n is an integer greater than or equal to 2, for example 2, 3, 4, 5, preferably greater than or equal to 6, for example 6, 7, 8, 9, 10, 11, 12, 13, 14, 15, 16, 17, 18 or greater than 18.

When the steps are not done simultaneously, they are generally followed by one or several washing steps.

A washing step makes it possible to eliminate the compounds not bonded to the spots or beads or to the various compounds bonded to said spots or beads.

Typically, a washing step consists of at least one cycle, preferably at least two cycles, more preferably 3 to 6 cycles, for distributing (for example, a volume of 400 µl) and aspirating a wash solution in each compartment or in the presence of each set of beads. Typically, the washing solution may be a Tris NaCl 0.01 M buffer, pH 7.4 doped with Tween 20 at 0.1%.

When the method is implemented with at least one solid support comprising at least two compartments, the compartments of the solid support or supports are preferably identical, in particular in terms of number and composition of the spots.

Alternatively, the method may be implemented with at least one solid support comprising at least two separate groups (or types) of compartments, each of the separate groups having a different number of spots and/or spot composition.

When the method is implemented with at least two sets of beads, the sets of beads can be identical, in particular in terms of number and composition of the beads.

Alternatively, the method may be implemented with at least two separate groups (or types) of sets of beads, in particular each of the separate groups of sets of beads having a different number and/or composition of beads.

Steps b), d), e) and f) are carried out in each compartment intended to analyze a sample or in each container containing a set of beads intended to analyze a sample.

Regarding step c), one sample is added per compartment or per container containing a set of beads.

The sample(s), the analytes, the additive(s), the control compound(s), the detection ligands of the analytes, the detection ligand(s) of the additive(s), the detection ligands of the control compound(s) and the reporter(s) are in particular as defined above in the corresponding paragraphs.

An additive used in the method according to the invention is an additive recognized by the capture ligand(s) of the deposition control of a detection ligand of an analyte.

A control compound present in the sample is a control compound recognized by the capture ligand(s) of the deposition control of a sample.

Each detection ligand of an analyte is specific to an analyte recognized by at least one capture ligand present in a detection spot of an analyte or on a detection bead of an analyte.

When step b) is not carried out simultaneously with one of steps c), d) or e), one or several washing steps can be carried out after step b) and before said steps c), d) and e) only when l is equal to 0.

When steps b), c), d) and e) are present, they can be carried out in any desired order: successively, or one, two or three of these steps simultaneously. However, when a step b) and a step d) respectively implement at least one additive and at least one detection ligand of said additive, said step d) is still done at the same time as or after said step b). Likewise, when a step e) is present, it is always done at the same time as or after step c), or before step c) as long as there is no washing step between steps e) and c). Furthermore, when step c) is done after a step b) in which l is greater than or equal to 1 and/or after a step d) in which l' is greater than or equal to 1 and/or after step e), no washing step is done between this or these steps and step c).

As an example, when steps b) to e) are present, they can be done simultaneously and/or successively, in the following orders: b) to e), b) c) e) d), c) b) d) e), c) b) e) d) or c) e) b) d).

Steps c), d) and/or e) can be done simultaneously with step b).

In one advantageous embodiment according to the invention, steps b) and c) are done simultaneously.

In another advantageous embodiment according to the invention, steps c) and d) are done simultaneously. It may indeed be advantageous to place the sample simultaneously in the presence of the detection ligands of the analytes, which interact better in solution with the analyte to which they are specific than when the analyte is already bonded to the capture antibody of the analyte.

In still another advantageous embodiment according to the invention, steps b), c) and d) are done simultaneously.

When several additives are used, the method may include one or several steps b) (and one or several steps d)), each of steps b) being able to be done independently before, after or at the same time as step c). There may for example be at least two steps b), one being done before or at the same time as step c), the other being done after or at the same time as step c).

The compounds of a given step may be provided in the form of a mixture, i.e., a solution, that comprises all of the compounds of that step and optionally the compounds of one or several steps done simultaneously.

When two or more than two steps are done simultaneously, the compounds of these different steps may be contributed in the form of one or several mixtures, i.e., one or several solutions, preferably in the form of a single mixture (i.e., a single solution).

For example, when steps b), c) and d) are done simultaneously, the additive(s) (when they are present), the l detection ligands of each of the p analytes to be detected, the detection ligand(s) of said additive(s) (when they are present), the l" detection ligands of each of the m analytes to be detected can be contributed in the form of a single mixture.

In one advantageous embodiment, l' is equal to n, i.e., at least n detection ligands of the n analytes are added in step d).

In certain embodiments, step e) is done after step c). This in particular involves the case where the presence of the or one of the detection ligands for a compound controls whether the sample risks causing interference at the same time.

For example, when the detection ligand of the control compound is a specific antibody of the transferrin and the sample comprises free transferrin, step e) is carried out after step c).

When step e) is carried out after step c), preferably at least one washing step of the compartments is done after step c) and before step e).

When the method according to the invention comprises step f), this step is always done after steps a) to e) and it is generally preceded by at least one washing step of the spots of each compartment or each set of beads.

The method may also comprise several steps f) if at least two deposition controls of a reporter are used, i.e., preferably one step f) per reporter.

When the method according to the invention comprises step g), this step is always done after a step f) and it is generally preceded by at least one washing step of the spots of each compartment or each set of beads.

The or at least one of the reporters of step f) is preferably both a reporter of an indirect detection marker coupled to at least one detection ligand of an analyte and that of a detection marker present in at least one control of the deposition of a reporter.

It may be advantageous for the controls used for the implementation of the multiplex analysis method according to the invention to mimic the different steps of the detection of analytes. For example, if the capture ligands of the analytes and the detection ligands of the analytes are antibodies, the detection ligand of the additive and, preferably, the detection ligand of the control compound are also antibodies. Likewise, the detection ligand of the additive and, preferably, the detection ligand of the control compound are marked with the same marker as that of the detection ligands of the analytes.

The method according to the invention generally comprises a step h) for detecting the signal corresponding to the detection markers of the control(s) (in particular the control spot(s) or the control bead(s)) and of the analyte(s).

A control is positive if a positive signal is detected at the end of the method.

A control is negative if no positive signal is detected at the end of the method.

The detection of a positive signal for each control used during the implementation of the method makes it possible to validate the entire method.

The absence of a signal at one or several controls means that one or several steps have not taken place correctly. In this case, the obtained results must not be used.

When a detection ligand of a control compound is deposited after the deposition of the sample and after at least one washing step, a negative control of the deposition of a sample means that the sample has not been deposited and/or that said detection ligand of a control compound has not been deposited.

The control of the deposition of a sample, the control of the deposition of a detection ligand of an analyte and, if applicable, the control of the deposition of a reporter are complementary and make it possible to ensure the proper performance of each of the steps of the method and make it possible to understand the origin of any flaw encountered in the analysis method.

The method according to the invention may also comprise:
 at least two steps b) and at least two steps d), when at least two controls of the deposition of a detection ligand of an analyte are used,
 at least two steps f), when at least two controls of the deposition of a sample are used, and/or
 at least two steps f), when at least two controls of the deposition of a reporter are used.

Use of One or Several Controls to Secure a Multiplex Analysis Method of a Sample.

The present invention also relates to the use of at least one control of the deposition of a sample and/or at least one control of the deposition of a detection ligand of an analyte, to secure a multiplex analysis of a sample.

Said use may further comprise the use of at least one control of the deposition of a reporter.

The present invention particularly relates to the use of at least one control selected from the group consisting of a control of the deposition of a sample, a control of the deposition of a detection ligand of an analyte and a control of the deposition of a reporter, to secure a multiplex analysis of a sample.

Here, "secure a multiplex analysis of a sample" means guaranteeing the reliability of the results of a multiplex analysis, in particular by avoiding the presence of "false negatives".

A "false negative" is a negative result reflecting the absence of one or several analytes to be detected in a sample, whereas said analyte(s) were present in the sample and should have been detected.

The present invention also relates to the use of at least two controls selected from the group consisting of a control of the deposition of a sample, a control of the deposition of a detection ligand of an analyte and a control of the deposition of a reporter, to secure a multiplex analysis of a sample.

The present invention particularly relates to the use of at least one control of the deposition of a sample, at least one control of the deposition of a detection ligand of an analyte and at least one control of the deposition of a reporter, to secure a multiplex analysis of a sample.

Said use is preferably done on a solid support comprising at least one compartment as defined above or on at least one set of beads as defined above.

The control of the deposition of a sample, the control of the deposition of a detection ligand of an analyte, the control of the deposition of a reporter and the sample are in particular as defined above.

The present invention also relates to a kit, characterized in that it comprises or consists of at least one solid support according to the invention and/or at least one set of beads according to the invention and, if applicable, at least one composition or solution to be used to carry out a multiplex analysis method according to the invention and/or user instructions.

Other features and advantages of the invention will better emerge through the following examples, provided as an illustration and non-limitingly. These examples and figures illustrate the invention without limiting its scope.

FIGURES

FIG. 1: Example of a solid support of the microplate type for a secure multiplex analysis. A shows a block diagram of a microplate including 18 wells. B diagrammatically shows the bottom of a well of the microplate. Each well of the microplate comprises 9 spots, 6 spots of which are each intended to detect one or several analytes making it possible to diagnose an infection (respectively A1, A2, A3, A4, A5 and A6) and 3 control spots: SDC (Sample Deposition Control), PVC (analyte detection ligand deposition control) and RVC (Reporter Deposition Control). C diagrammatically shows the three control spots comprising the detection antibodies bonded to the solid phase (PS). Ac CC: Detection antibody of the control compound. Ac Add: Detection antibody of the additive. MS+B: Carrier molecule marked with biotin.

Figure 2:
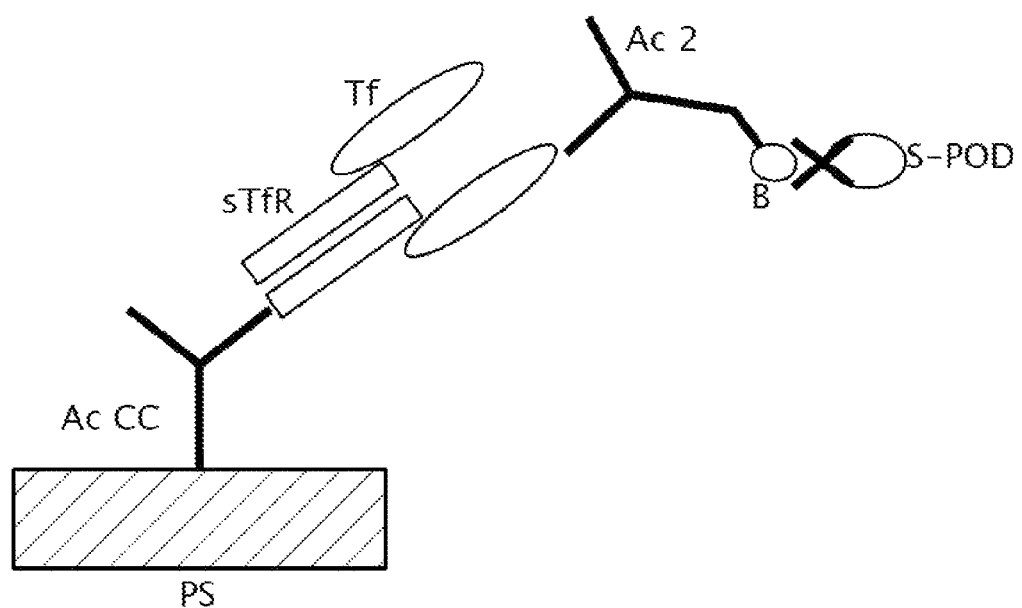

FIG. 2: Diagram of a positive control of the deposition of a sample (SDC) in heterologous format. The control of the deposition of a sample comprises the capture antibody of the control compound fixed to the solid phase (PS). The capture antibody here is specific to the soluble receptor of the transferrin (sTfR). The control compound, here complex 2:2 soluble transferrin receptor (sTfR):transferrin (Tf) is fixed to the capture antibody at the control of the deposition of a sample and to the detection antibody (Ac 2) that is specific to the transferrin. The detection antibody (Ac 2) is marked with biotin (B). The developing is done by adding streptavin coupled to a peroxidase (S-POD), then the substrate of this enzyme (not shown). The capture antibody and the detection antibody can be monoclonal or polyclonal antibodies. In all cases, it involves a heterologous sandwich.

Figure 3:
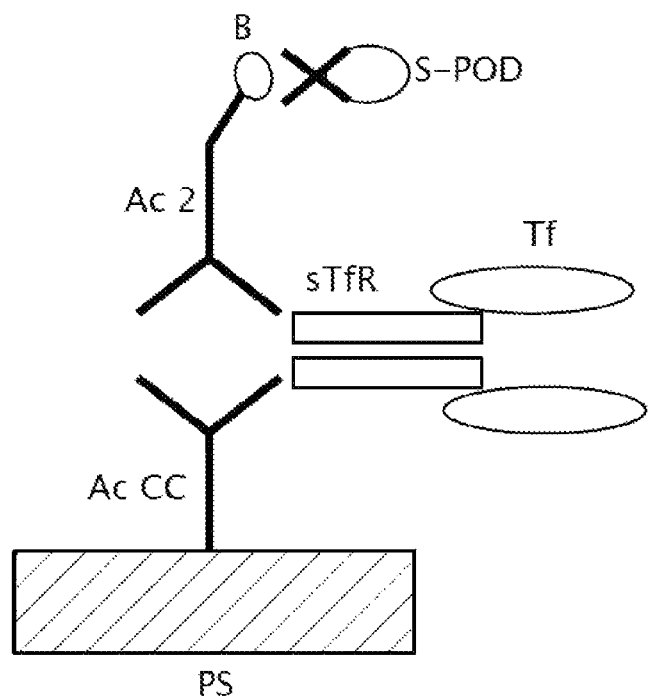

FIG. 3: Diagram of a positive control of the deposition of a sample (SDC) in homologous format. The control of the deposition of a sample comprises the capture antibody of the control compound fixed to the solid phase (PS). The capture antibody here is specific to the soluble receptor of the transferrin (sTfR). The control compound, here complex 2:2 soluble transferrin receptor (sTfR): transferrin (Tf) is fixed to the capture antibody at the control of the deposition of a sample and to the detection antibody (Ac 2) that is also specific to the soluble transferrin receptor (sTfR). The detection antibody (Ac 2) is marked with biotin (B). The developing is done by adding streptavin coupled to a peroxidase (S-POD), then the substrate of this enzyme (not shown). The capture antibody and the detection antibody are for example monoclonal antibodies. In involves a homologous sandwich.

Figure 4:
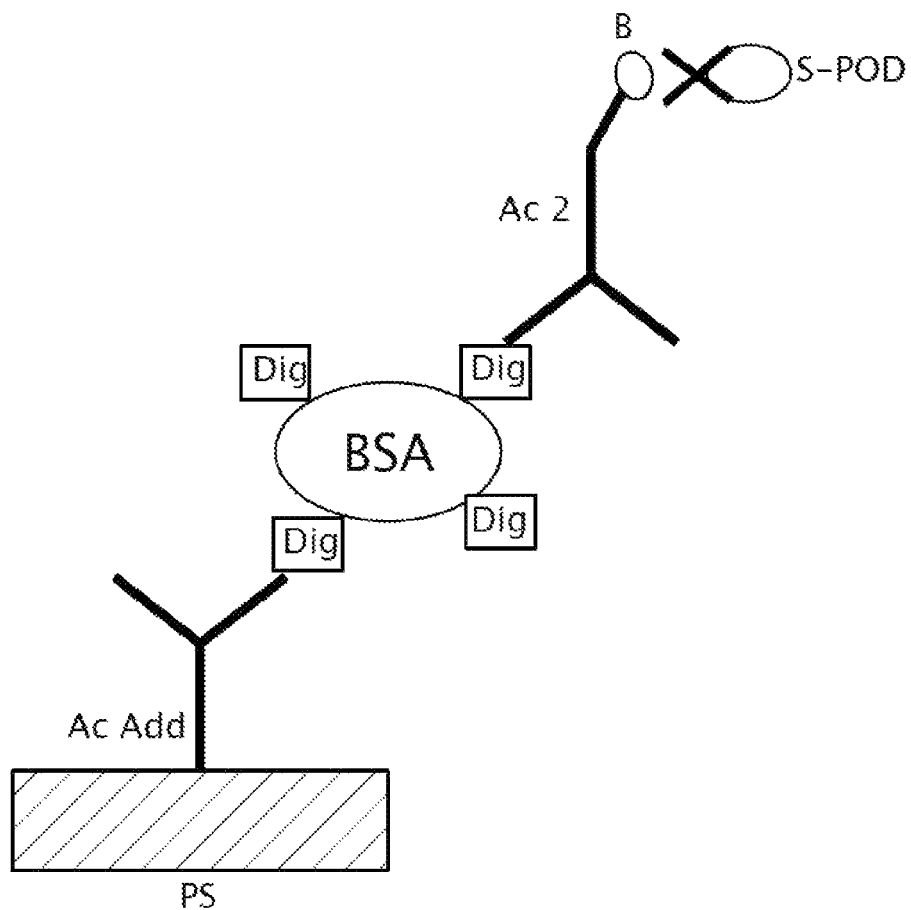

FIG. 4: Diagram of a positive control of the deposition of a detection ligand of an analyte (PVC) The method control comprises the capture antibody of the additive fixed to the solid phase (PS). The capture antibody here is specific to digoxigenin (Dig). The additive comprises digoxigenin and BSA, the digoxigenin being complexed to the BSA. The additive is bonded via the digoxigenin to the capture antibody at the control of the deposition of a detection ligand of an analyte and to the detection antibody (Ac 2). The detection antibody (Ac 2) is marked with biotin (B). The developing is done by adding streptavin coupled to a peroxidase (S-POD), then the substrate of this enzyme (not shown). The capture antibody and the detection antibody can both be monoclonal antibodies or both polyclonal antibodies, in which case it involves a homologous sandwich. The capture antibody can be a monoclonal antibody and the detection antibody a polyclonal antibody, or vice versa, in which case it involves a heterologous sandwich.

Figure 5:
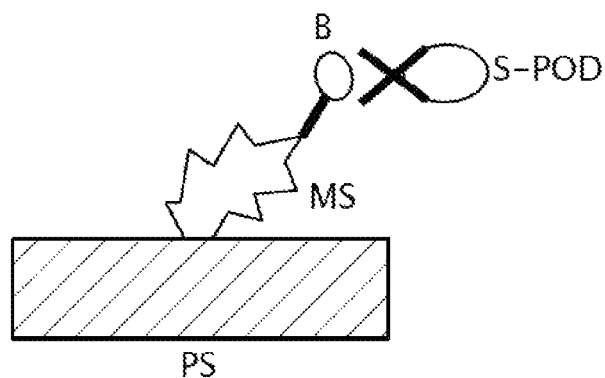

FIG. 5: Diagram of a positive control of the deposition of a reporter (RVC). The control of the deposition of a reporter comprises a carrier molecule (MS) coupled to biotin (B) fixed to the solid phase (PH). The developing is done by adding streptavin coupled to a peroxidase (S-POD), then the substrate of this enzyme (not shown).

Figure 6:
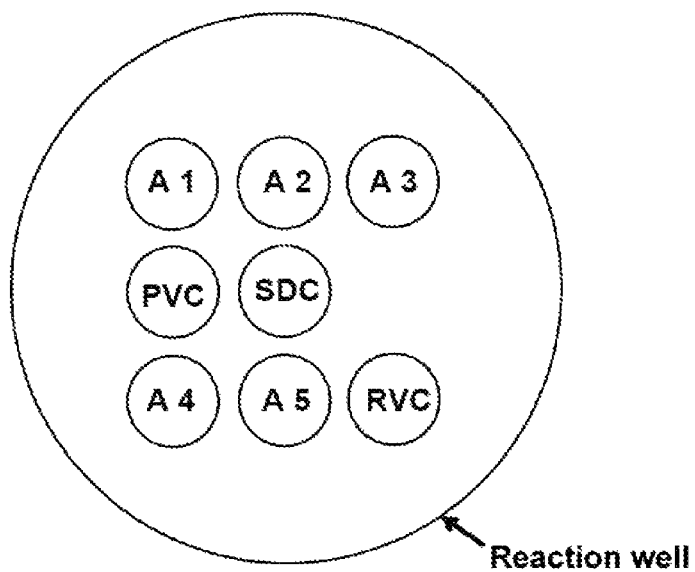

FIG. 6: "Spotting" grid situated at the bottom of a well of a microplate and including the spots of 5 analytes to be assayed (A1 to A5) and the three control spots SDC, PVC and RVC.

Figure 7:
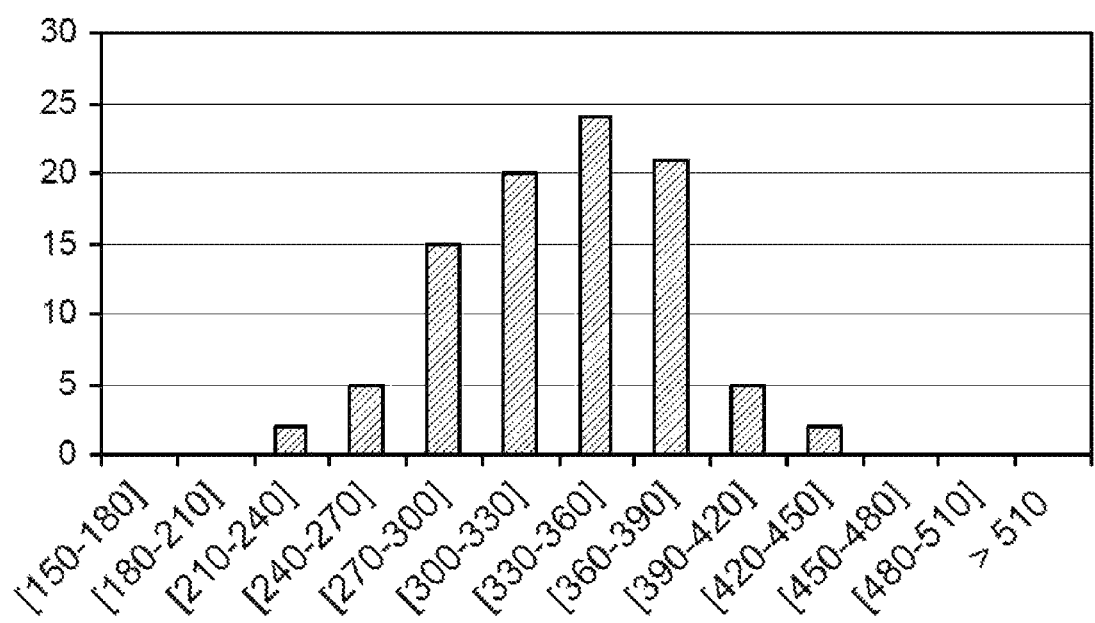

FIG. 7: Distribution of the signal of the SDC control beads in simplex format of a population of 94 samples. The Y-axis shows the number of samples and the X-axis shows intervals of Relative Fluorescence Intensity (RFI).

Figure 8:
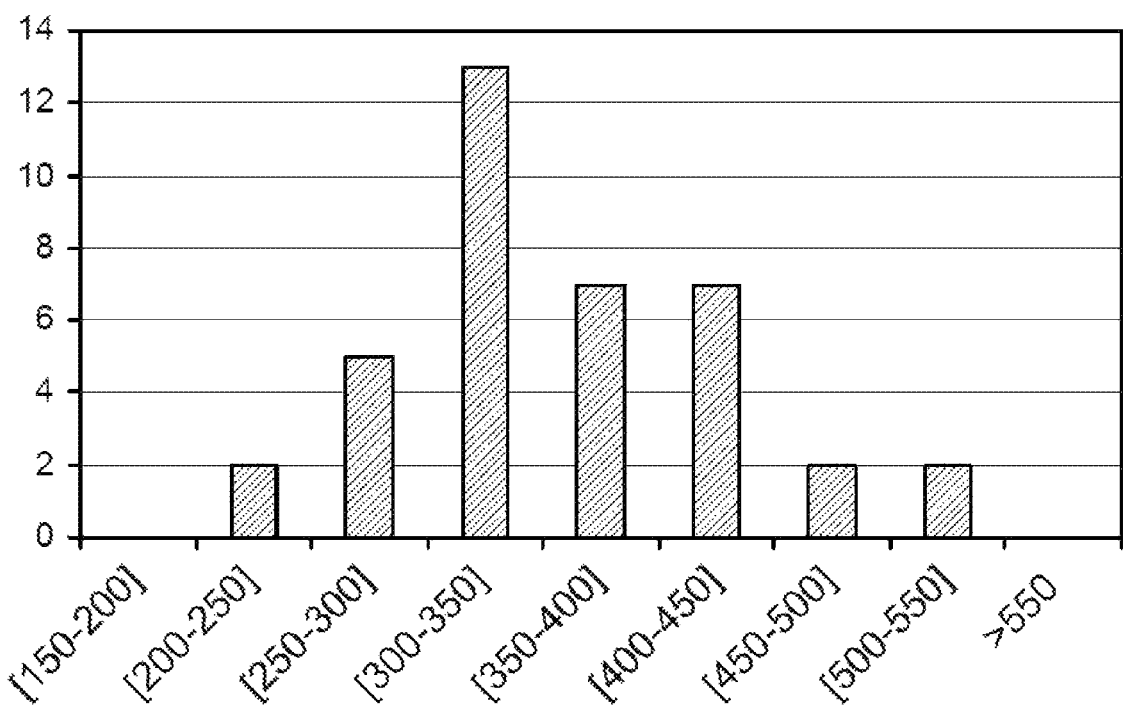

FIG. 8: Distribution of the signal of the PVC control beads in simplex format of a population of 38 samples. The Y-axis shows the number of samples and the X-axis shows intervals of Relative Fluorescence Intensity (RFI).

EXAMPLES

Example 1

"Liquid Chip" Method

Principle

The two controls described in this example make it possible to validate (cf. table 1):
- for the SDC ("Sample Deposit Control" or "Control of the deposition of a sample"): the deposition of the sample and also step 2 (deposition of the conjugates 2, i.e., the detection ligands deposited in step 2) and step 3) (deposition of the S-PE reporter: streptavidin coupled to Phycoerythrin), and
- for the PVC ("Process Verification Control" or "control of the deposition of a detection ligand of an analyte"): the deposition of step 1 (deposition of the conjugates 1, i.e., the detection ligands deposited in step 1) and also step 2 (deposition of the conjugates 2, in dotted lines because not illustrated in this example) and step 3) (deposition of the S-PE reporter).

TABLE 1

| | Steps controlled by the SDC and PVC controls | | | |
|---|---|---|---|---|
| | Sample | Conjugates 1 (step 1) | Beads (step 1) | Conjugates 1 (step 2) | S-PE (step 3) |
| SDC | | | | | |
| PVC | | | | | |

Materials (i) Analysis System

The BioPlex 200® analyzer (Bio-Rad, Marnes-la-Coquette, France) is used according to the manufacturer's instructions. This immunoanalysis machine contains a flow cytometer and a Luminex 100™ detector (Luminex Corp., Austin, Tex., United States) and uses heterogeneous sets of superparamagnetic particles. Each homogenous group of particles, polystyrene compounds and methacrylic acid (COOH function), and having a size of 8 μm in diameter, is manufactured with different percentages of fluorochromes (CL1 and CL2) producing a unique identification code assigned to each group of particles and detectable by the laser of the Luminex 100™ detector (Luminex Corp., Austin, Tex., United States). After the immunological reaction, the beads of one set pass one by one through a flow cell, at the center of a liquid sheath, to be simultaneously excited and read by two separate lasers. The measurements are done upon the passage of each bead.

The laser with a 638 nm red ray excites the identification fluorochromes (CL1 and CL2) encrusted in the surface of each particle and the composite signal is interpreted to identify the analyte detected by the particle. This laser therefore serves, by identifying the particle category, to identify the test in progress.

The laser with a 532 nm green ray excites the S-PE (streptavidin coupled with Phycoerythrin) reporter and the emitted fluorescence is proportional to the quantity of reporter fixed on the particle. This laser therefore serves to measure the reactivity of the analyte immobilized on said particle.

The software of the system converts the signal related to the presence of the detection ligand into a relative fluorescence intensity (RFI) value. A ratio may be calculated in order to rate the result qualitatively, as positive or negative.

(ii) Solid Phase (Beads)

A set of beads including six separate groups of Luminex™ superparamagnetic particles (Luminex Corp., Austin, Tex., United States) is used. This set of beads comprises a group of beads for controlling the deposition of a sample (SDC beads), a group of beads for controlling the deposition of a detection ligand of an analyte (PVC beads) and 4 groups of beads for detecting an analyte (analytes to be assayed: A1, A2, A3 and A4).

Each group of particles is coated with a specific capture ligand of a particular test. Each capture ligand is coupled using a hetero-bifunctional reagent.

The SDC beads are covered with a soluble anti-receptor mouse monoclonal antibody of the Transferrin (Fitzgerald, United States) immobilized at 1 μg/mg of particles.

The PVC beads are covered with an anti-Digoxigenin sheep polyclonal antibody (Abcam, United States) immobilized at 5 μg/mg of particles.

The detection beads of the analytes A1, A2, A3 and A4 are covered with one or several specific capture ligands of the analytes to be detected.

(iii) Detection Ligands

The detection ligand of the control compound (the SDC control), pAb-anti-Tf-biot, is an anti-Transferrin sheep polyclonal antibody (Bio-Rad, Barnes la Coquette, France) coupled to biotin (Thermo Scientific, France) using a hetero-bifunctional reagent known in itself by those skilled in the art.

The detection ligand of the additive (of the PVC control), pAb-anti-DIG-biot, is an anti-Digoxigenin sheep polyclonal antibody (Abcam, France) coupled to biotin (Pierce, United States) using a hetero-bifunctional reagent known in itself by those skilled in the art.

(iv) Additive

The BSA-DIG additive is Digoxigenin (Sigma, France) grafted on a carrier molecule, in this example Bovine Serum Albumin (Millipore, France), using a hetero-bifunctional reagent known in itself by those skilled in the art.

(v) Reporter

The S-PE reporter is streptavidin (Roche, Germany) coupled to the Phycoerythrin (Cyanotech, Hawaii, United States), using a hetero-bifunctional reagent known in itself by those skilled in the art.

(vi) Diluents vi.1. Diluent of the Superparamagnetic Particles

Tris buffer solution 50 mM, pH 7.5, containing: NaCl 150 mM, EDTA 20 mM, Bovine Serum Albumin at 10%, mouse IgG (Meridian, United States) at 500 μg/mL, Octyl-n-Glucoside at 0.10%, NaN3 at 0.095%.

vi.2. Diluent of Conjugates 1

Tris buffer solution 50 mM, pH 7.5, containing: NaCl 150 mM; EDTA 20 mM, Chaps 0.1%, Glycerol 10%, NaN3 at 0.095%.

vi.3. Diluent of Conjugates 2

Citrate buffer solution 50 mM, pH 6.7, containing: NaCl 150 mM, EDTA 5.6 mM, Bovine Serum Albumin at 1%, Triton at 2%, Sheep serum at 10%, mouse IgG (Meridian, United States) at 500 μg/mL, Proclin 300™ (trademark of the company Supelco) at 0.5%, cow's milk (100% skim) at 15%, Glycerol 10%, NaN3 at 0.095%.

vi.4. Diluent of the S-PE Reporter

Phosphate buffer, pH 7.4 containing: NaCl 150 mM, Tween 20™ (trademark of the company Sigma) at 0.1%, Proclin 300™ (trademark of the company Supelco) at 0.5%, PEG 6000 2.75%, Bovine Serum Albumin 1%, Normal Sheep Serum 1%, NaN3 at 0.095%.

vi.5. Washing Solution

Tris 10 mM buffer solution, pH 7.4, containing: NaCl 218 mM, Tween 20™ (trademark of the company Sigma) at 0.1%, Proclin 300™ (trademark of the company Supelco) at 0.002%.

(vii) Reaction Dishes

The immunological reactions take place in the wells of 96-well microplates made from poly propylene having a maximum volume of 355 μL per well.

(viii) Samples

The negative samples (serum or plasma) used come from the French blood agency in Lille.

Methods

The multiplex format test protocol comprises assaying 4 different analytes, the assay of analytes A1 and A2 being done in one immunological time, the assay of analytes A3 and A4 being done in two immunological times.

The format of the tests is shown in FIGS. 2 and 4, in which S-PE is used in place of S-POD.

Step 1:

1. In each well of a microplate are successively distributed:

+100 μL of sample

+25 μl of diluent of the conjugates 1 containing:

+/− BSA-DIG

+/− the detection ligands of analytes A1 and A2

+25 μL of immunoreactive superparamagnetic particles (mixture of particles, 1.2 μg per type of beads: SDC, PVC+/− beads of the analytes to be assayed)

2. The mixture is incubated for 40 minutes at 37° C. with agitation.

3. The following washing steps are carried out: separation of the solid and liquid phases by magnetization and 3 successive washes with at least 300 μl of wash solution. In the last wash, the particles are put back in suspension.

Step 2:

4. Distributed in each reaction well is 90 μl of diluent of conjugates 2 containing:

+/− the detection ligand of the pAb-anti-Tf-biot control compound

+/− the detection ligand of the pAb-anti-DIG-biot additive

+/− the detection ligands of analytes A3 and A4

5. The mixture is incubated for 15 minutes at 37° C. with agitation.

6. The wash steps (idem point 3) are carried out.

Step 3:

7. 90 µL of the S-PE reporter is distributed in each reaction well.

8. The mixture is incubated for 15 minutes at 37° C. with agitation.

9. The wash steps (idem point 3) are carried out.

10. The particles are put back in suspension in each reaction well while adding 120 µL of washing solution, then the microplate is agitated.

11. The suspension of particles in each well is aspirated by the flow cytometer.

12. The suspension of particles in each well is read using two laser rays.

13. The results of the readings are processed directly by the flow cytometer and recorded in Relative Fluorescence Intensity (RFI) units.

14. To interpret the results, for each sample, a ratio is calculated with respect to a threshold value ("cutoff").

Calculation of the Ratio

The SDC ratio of the samples is calculated as follows:

$$\text{Sample SDC ratio} = \frac{RFI \text{ signal of the sample}}{SDC \text{ threshold value}}$$

Likewise, the PVC ratio of the samples is calculated as follows:

$$\text{Sample PVC ratio} = \frac{RFI \text{ signal of the sample}}{PVC \text{ threshold value}}$$

The samples having ratios (SDC or PVC) above 1 are declared "valid"; those for which the ratios are below 1 are declared "not valid".

The SDC and PVC threshold value has been established according to a statistical study described in the results below.

Results (i) SDC System in Simplex Format

In the system, the detection beads of analytes A1 to A4 and their detection ligands are not used.

The study of 94 samples makes it possible to determine the threshold value of the SDC system (cf. FIG. 7). The threshold value of the SDC system is calculated by subtracting 3 times the standard deviation of the signal of the sample population from the average value of the signal of the population.

TABLE 2

Statistics of the SDC signal for the population of 94 samples and calculation of the threshold value

| | |
|---|---|
| Average (RFI) | 334 |
| Standard deviation (σ) (RFI) | 44.02 |
| Variation coefficient (CV) in % | 13.2% |
| Maximum of the population (RFI) | 427 |
| Minimum of the population (RFI) | 239 |
| Threshold value = Average − 3 σ (RFI) | 201.5 |

The response of the SDC system is measured in the case of a nominal method (Deposited volume of sample=100 µL, Conjugates 2 volume=90 µL, S-PE volume=90 µL) (case no. 1 of table 3). Cases 2, 3, 4 of table 3 are downgraded methods: case 2=absence of sample deposition, case 3=absence of deposition of conjugates 2, case 4=absence of S-PE deposition.

In this case, the mixture comprising the "conjugates 2" comprises 90 µL of diluent of the conjugates 2 containing the detection ligand of the pAb-anti-Tf-biot control compound.

TABLE 3

Summary of the SDC ratios obtained during a nominal method (case 1) and downgraded methods (cases 2, 3 and 4)

| Case | Sample Volume (µL) | Conjugates 2 Volume (µL) | Volume S-PE (µL) | RFIs* | SDC ratio | Status VALID/NOT VALID |
|---|---|---|---|---|---|---|
| 1 | 100 | 90 | 90 | 331 | 1.6 | VALID |
| 2 | 0 | 90 | 90 | 31 | 0.2 | NOT VALID |
| 3 | 100 | 0 | 90 | 29 | 0.1 | NOT VALID |
| 4 | 100 | 90 | 0 | 29 | 0.1 | NOT VALID |

*RFIs: Relative Fluorescence Intensities

Cases 2, 3, 4 lead to SDC ratios lower than 1, which makes it possible to invalidate the measurements from these downgraded methods.

(ii) Impact of the SDC System on Performance in Multiplex Format

In the SDC system in multiplex format (MPX), the detection beads of analytes A1 to A4 and the corresponding detection ligands are used.

By comparing the RFI signals obtained between a MPX format without SDC versus MPX with SDC (cf. table 4), the addition of a SDC format does not affect the performance of a multiplex including 4 analytes (i.e., the deviations in % between the RFI signals of a MPX format without SDC versus MPX with SDC are comprised in an interval +/−20%, which is considered statistically acceptable).

TABLE 4

Comparison in % of the RFI signals obtained between a MPX format without SDC versus a MPX format with SDC

| | Number of samples used for the calculations | Analyte 1 | Analyte 2 | Analyte 3 | Analyte 4 |
|---|---|---|---|---|---|
| Standard deviation in % between the RFI signal measured in MPX without | 4 positive samples Analyte 1 | −5.2% | | | |
| | 3 positive samples Analyte 2 | | −3.0% | | |
| | 5 positive samples Analyte 3 | | | −2.2% | |

TABLE 4-continued

Comparison in % of the RFI signals obtained between a MPX format without SDC versus a MPX format with SDC

|  | Number of samples used for the calculations | Analyte 1 | Analyte 2 | Analyte 3 | Analyte 4 |
|---|---|---|---|---|---|
| SDC versus MPX with SDC | 2 positive samples Analyte 4 |  |  |  | −19.9% |
|  | 32 negative samples for the 4 Analytes | 0.1% | 1.3% | −0.1% | −2.5% |

(iii) PVC in Simplex Format

As before, in this format, the detection beads of analytes A1 to A4 and the corresponding detection ligands are not used.

The study of 38 samples makes it possible to determine the threshold value of the PVC system (cf. FIG. 8).

The threshold value of the PVC system is calculated by subtracting 3 times the standard deviation of the signal of the sample population from the average value of the signal of the population (cf. table 5).

TABLE 5

Statistics of the PVC signal for the population of 38 samples and calculation of the threshold value

| Average (RFI) | 356 |
|---|---|
| Standard deviation (σ) (RFI) | 70.92 |
| Variation coefficient (CV) in % | 19.9% |
| Maximum of the population (RFI) | 510 |
| Minimum of the population (RFI) | 222 |
| Threshold value = Average − 3 σ (RFI) | 143.4 |

The response of the PVC system is measured in the case of a nominal method (Deposited volume of sample=100 µL, Conjugates 1 volume=90 µL, S-PE volume=90 µL) (case no. 1 of table 6). Cases 2, 3 of table 6 are downgraded methods: case 2=absence of conjugates 1 deposition, case 3=absence of S-PE deposition.

TABLE 6

Summary of the PVC ratios obtained during a nominal method (case 1) and downgraded methods (cases 2, 3)

| Case | Conjugates 1 Volume (µL) | Volume S-PE (µL) | RFIs* | Ratio | Status VALID/NOT VALID |
|---|---|---|---|---|---|
| 1 | 90 | 90 | 356 | 2.5 | VALID |
| 2 | 0 | 90 | 93 | 0.6 | NOT VALID |
| 3 | 90 | 0 | 30 | 0.2 | NOT VALID |

Cases 2 and 3 lead to PVC ratios lower than 1, which makes it possible to invalidate the measurements from these downgraded methods.

(iv) Impact of the Simplex Versus Multiplex Mode on the Performance of the PVC System In the PVC system in multiplex format, the detection beads of analytes A1 to A4 and the corresponding detection ligands are used.

The performance of the PVC system is similar in simplex mode and multiplex mode (cf. table 7).

TABLE 7

Comparison of the PVC performance in simplex versus multiplex mode

|  | 4 Analytes, PVC (multiplex) | PVC (simplex) |
|---|---|---|
| Average RFI of 38 samples (RFI) | 356 | 320 |
| CV (%) | 19.9% | 20.6% |
| Max (RFI) | 510 | 472 |
| Min (RFI) | 222 | 194 |
| Threshold value = Average − 3 σ (RFI) | 143.4 | 121.7 |

Furthermore, by comparing the RFI signals obtained between a MPX format without SDC or PVC versus a MPX format with SDC and PVC, it appears that the addition of SDC and PVC tests does not affect the performance of a multiplex including 4 analytes to be assayed (i.e., the deviations in % between the RFI signals of a MPX format without SDC or PVC versus a MPX format with SDC and PVC are comprised in an interval +/−20%, which is considered statistically acceptable).

Example 2

Spotting Method

Materials and Methods

The three controls described in this example make it possible to validate (cf. table 8):

for the SDC ("Sample Deposit Control" or "control of the deposition of a sample"): the deposition of the sample and also step 2 (deposition of the conjugates 2), step 3 (deposition of the S-POD reporter) and step 4 (deposition of the Luminol substrate).

for the PVC ("Process Verification Control" or "control of the deposition of a detection ligand of an analyte"): the depositions of step 1 (deposition of the additive and deposition of the conjugates 1), step 3 (deposition of the S-POD reporter) and step 4 (deposition of the Luminol substrate), and for the RVC ("Revelation Verification Control" or "control of the deposition of a reporter"): the revelation step, by controlling both step 3 (deposition of the S-POD reporter) and step 4 (deposition of the Luminol substrate).

TABLE 8

Steps controlled by the SDC, PVC and RVC controls

| | Sample | Additive (step 1) | conjugates 1 (step 1) | Conjugates 2 (step 2) | S-POD (step 3) | Luminol (step 4) |
|---|---|---|---|---|---|---|
| SDC | | | | | | |
| PVC | | | | | | |
| RVC | | | | | | |

Materials (i) Analysis System

The technology used for this system is an innovative nanospotting on biochip multiplex technology (cf. definition below), with developing by chemiluminescence owing to a reporter marked by the enzyme of the horseradish peroxidase and developed by a substrate of the luminol type.

The term "biochip" is a collection of miniaturized test sites (or "micro-array") arranged on a solid support that makes it possible to perform many tests at the same time in order to obtain a faster rhythm.

Within each well of a microplate (Greiner, Germany), a spotter robot is used to deposit 50 nL drops of a protein solution containing proteins or antibodies specific to the analyte to be assayed (A1, A2, A3, A4, A5, SDC, RVC and PVC) (cf. FIG. 6). The bottom of each well of these microplates has protein and peptide adsorption capacities known in themselves by those skilled in the art. The spots thus obtained are saturated with a saturation solution known in itself by those skilled in the art.

It is next possible to perform a traditional immunological reaction in 1 or 2 immunological times within these biochips.

After the immunological reaction, the addition of the developing substrate causes a light emission. Indeed, the oxidation of the luminol by enzymatic catalysis leads to a light emission proportional to the quantity of Streptavidin-peroxidase reporter fixed by the spot. The acquisition of the signal is done by a scientific camera. The resulting image is then analyzed in order to determine the intensity of the luminescence produced by each geographical zone of the bottom of the well corresponding to each spot (addressing information).

The software of the system converts the signal measured by spot into a value in Relative Luminescence Units (RLU). A ratio may be calculated in order to rate the result qualitatively, as positive or negative, as outlined below.

(ii) Solid Phase (Spots)

The different control spots are:
- the SDC spot, comprising a soluble anti-receptor mouse monoclonal antibody of the Transferrin (Fitzgerald, United States) immobilized at 50 μg/mL,
- the PVC spot, comprising a soluble anti-Digoxigenin mouse monoclonal antibody (Covalab, France) immobilized at 25 μg/mL, and
- the RVC spot comprising an anti-KLH (Keyhole Limpet Hemocyanin) mouse monoclonal antibody (Genway, United States) coupled to biotin (Thermo Scientific, France) using a hetero-bifunctional reagent known in itself by those skilled in the art and immobilized at 1 μg/mL.

(iii) Detection Ligands

The detection ligand of the control compound (relative to the SDC control), pAb-anti-Tf-biot, is an anti-Transferrin sheep polyclonal antibody (Bio-Rad, Barnes la Coquette, France) coupled to biotin (Thermo Scientific, France) using a hetero-bifunctional reagent known in itself by those skilled in the art.

The detection ligand of the additive (relative to the PVC control), mAb-anti-DIG-biot, is an anti-Digoxigenin mouse monoclonal antibody coupled to biotin (Covalab, France).

(iv) Additive

The BSA-DIG additive is Digoxigenin (Sigma, France) grafted on a carrier molecule, in this example Bovine Serum Albumin (Millipore, France). The coupling is done using a hetero-bifunctional reagent known in itself by those skilled in the art.

(v) Reporter

The S-POD reporter is streptavidin (Roche, Germany) coupled with Peroxidase (Roche Germany) according to the method described by P. Nakane and A. Kawaoi [J Histochem Cytochem (1974) Vol. 22, No. 12. pp. 1084-1091), known in itself by those skilled in the art.

(vi) Diluents a) Diluent of the Additive

Tris buffer solution 50 mM, pH 7.5, containing: NaCl 150 mM, EDTA 20 mM, mouse IgG (Meridian, United States) at 500 μg/mL, Cow's milk (100% skim) at 15%, Sheep serum at 10%, NaN3 at 0.095%.

b) Diluent of conjugates 1

Tris buffer solution 50 mM, pH 7.5, containing: NaCl 150 mM; EDTA 20 mM, Chaps 0.1%, Glycerol 10%, NaN3 at 0.095%.

c) Diluent of conjugates 2

Citrate buffer solution 50 mM, pH 6.7, containing: NaCl 150 mM, EDTA 5.6 mM, Triton at 2%, Sheep serum at 10%, mouse IgG 500 μg/mL, Proclin 300™ (trademark of the company Supelco) at 0.5%, cow's milk (100% skim) at 15%, Glycerol 10%. NaN3 at 0.095%.

d) Diluent of the S-POD Reporter

Citrate buffer solution 50 mM, pH 6.7, containing: NaCl 2053 mM, Tween 20™ (trademark of the company Sigma) at 0.5%, Proclin 300™ (trademark of the company Supelco) at 0.5%, cow's milk (100% skim) at 7%, Glycerol 20%.

e) Wash Solution

Tris 10 mM buffer solution, pH 7.4, containing: NaCl 218 mM, Tween 20™ (trademark of the company Sigma) at 0.1%, Proclin 300™ (trademark of the company Supelco) at 0.002%.

f) Developing Substrate

The ELISTAR ETA C Ultra ELISA developing substrate (Cyanagen, Italy) is made up of two solutions: XLSE024L Luminol enhancer solution (A) and XLSE024P Peroxide solution (B).

(vii) Reaction Dishes

The immunological reactions take place in 96-well microplates made from polystyrene having a maximum volume of 392 μL per well.

(viii) Samples

The negative samples (serum or plasma) used come from the French blood agency in Lille.

Methods

The test protocol comprises the following steps.

Step 1:

1. In each well of a microplate (comprising the spots) are successively distributed:
+20 μl of diluent of the additive containing the BSA-DIG additive
+20 μl of diluent of the conjugates 1 comprising:
  + the detection ligand of the mAb-anti-DIG-biot additive, and
  + the detection ligands of analytes 1, 2 and 3 to be assayed +40 µl of sample 2. The mixture is incubated for 40 minutes at 37° C. with agitation.

3. Three successive washes with at least 400 µl of wash solution are done.

Step 2:

4. Distributed in each reaction well is 50 µl of diluent of conjugates 2 containing:

+ the detection ligand of the pAb-anti-Tf-biot control compound

+ the detection ligands of analytes 4 and 5 to be assayed.

5. The mixture is incubated for 15 minutes at 37° C. with agitation.

6. The wash steps (idem point 3) are carried out.

Step 3:

7. 50 µL of the S-POD reporter is distributed in each reaction well.

8. The mixture is incubated for 15 minutes at 37° C. with agitation.

Step 4:

9. 25 µL of developing solution "B" is distributed in each reaction well.

10. 25 µL of developing solution "A" is distributed in each reaction well.

10. The mixture is incubated for 1 minute at 37° C. with agitation.

11. The acquisition of the luminescence signal is done for 180 seconds.

12. The results of the readings are processed directly by an image analysis system and recorded in Relative Light Units (RLU).

13. To interpret the results, for each sample, a ratio is calculated with respect to a threshold value (or "cutoff").

Calculation of the Ratio

Two Analysis Modes are Illustrated Below:

Analysis Mode 1: A Single Threshold Value

The SDC ratio of the samples is calculated as follows:

$$\text{Sample } SDC \text{ ratio} = \frac{RLU \text{ signal of the sample}}{SDC \text{ threshold value}}$$

Likewise, the PVC ratio of the samples is calculated:

$$\text{Sample } PVC \text{ ratio} = \frac{RLU \text{ signal of the sample}}{PVC \text{ threshold value}}$$

Similarly, the RVC ratio of the samples is calculated:

$$\text{Sample } RVC \text{ ratio} = \frac{RLU \text{ signal of the sample}}{RVC \text{ threshold value}}$$

The samples having ratios (SDC or PVC or RVC) above 1 are declared "valid"; those for which the ratios are below 1 are declared "not valid". The SDC, PVC and RVC threshold value has been established according to a statistical study described in the results chapter below.

Analysis Mode 2: Two Threshold Values

Two SDC ratios of the samples are calculated as follows:

$$\text{Sample } SDC \text{ ratio (threshold}-) = \frac{RLU \text{ signal of the sample}}{SDC \text{ (threshold}-) \text{ value}}$$

$$\text{Sample } SDC \text{ ratio (threshold}+) = \frac{RLU \text{ signal of the sample}}{SDC \text{ (threshold}+) \text{ value}}$$

Likewise, the PVC ratios of the samples are calculated:

$$\text{Sample } PVC \text{ ratio (threshold}-) = \frac{RLU \text{ signal of the sample}}{PVC \text{ (threshold}-) \text{ value}}$$

$$\text{Sample } PVC \text{ ratio (threshold}+) = \frac{RLU \text{ signal of the sample}}{PVC \text{ (threshold}+) \text{ value}}$$

Similarly, the RVC ratios of the samples are calculated:

$$\text{Sample } RVC \text{ ratio (threshold}-) = \frac{RLU \text{ signal of the sample}}{RVC \text{ (threshold}-) \text{ value}}$$

$$\text{Sample } RVC \text{ ratio (threshold}+) = \frac{RLU \text{ signal of the sample}}{RVC \text{ (threshold}+) \text{ value}}$$

The samples having ratios (threshold−) (SDC or PVC or RVC) above 1 are declared "valid"; those for which the ratios are below 1 are declared "not valid".

The samples having ratios (threshold+) (SDC or PVC or RVC) below 1 are declared "valid"; those for which the ratios are above 1 are declared "not valid".

The SDC, PVC and RVC threshold value has been established according to a statistical study described in the results chapter below.

Results

The multiplex described in this example includes 5 analytes to be assayed, 3 analytes whereof the detection ligands are added in step 1 (A1, A2 and A3), 2 analytes whereof the detection ligands are added in step 2 (A4 and A5) and the three SDC, PVC and RVC controls.

Table 9 groups together the scenarios that may be encountered upon isolated or cumulative invalidation of the SDC, PVC and RVC controls.

The responses of the SDC, PVC and RVC controls are measured in the case of a nominal method (Additive Volume=20 µL, Conjugates 1 Volume=20 µL, Deposited Sample Volume=40 µL, Conjugates 2 Volume=50 µL, S-POD Volume=50 µL, Luminol Volume=25 µL solution B+25 µL solution A) for 22 samples.

The study of these 22 samples makes it possible to characterize the SPC, PVC, RVC response in terms of average spots, standard deviation, minimum and maximum value (cf. table 10a and 10b). The threshold values of the SDC, PVC and RVC controls are also calculated.

TABLE 9

Interpretation of all of the SDC, PVC and RVC controls and identification of the deficient step in the method.

| SDC Status VALID/ NOT VALID | PVC Status VALID/ NOT VALID | RVC Status VALID/ NOT VALID | SDC and PVC and RVC Status VALID/NOT VALID | Deficient step at the source of the invalidation of the method |
|---|---|---|---|---|
| NOT VALID | VALID | VALID | NOT VALID | Sample deposition or deposition of detection ligands in step 2 |
| VALID | NOT VALID | VALID | NOT VALID | Additive deposition or deposition of detection ligands in step 1 |
| NOT VALID | NOT VALID | VALID | NOT VALID | Sample deposition or deposition of detection ligands in step 2 and Additive deposition or deposition of detection ligands in step 1 |
| NOT VALID | NOT VALID | NOT VALID | NOT VALID | S-POD or Luminol deposition Furthermore, in this scenario, the sample, additive, detection ligands of step 1, detection ligands of step 2 depositions cannot be validated or invalidated. |
| VALID | VALID | NOT VALID | Cases unable to arise | An not valid RVC signal involves an invalidation of the SDC and PVC |
| NOT VALID | VALID | NOT VALID | | |
| VALID | NOT VALID | NOT VALID | | |

Analysis Mode 1: A Single Threshold Value

TABLE 10a

Response of the SDC, PVC and RVC controls (average response, standard deviation, minimum and maximum value, threshold values)

|  | SDC | PVC | RVC |
|---|---|---|---|
| Average response (RLUs) | 998 | 2623 | 3200 |
| Standard deviation ($\sigma$) (RLUs) | 124 | 154 | 214 |
| Variation coefficient (CV) in % | 12.4% | 5.9% | 6.7% |
| Maximum of the population (RLUs) | 1246 | 2997 | 3535 |
| Minimum of the population (RLUs) | 798 | 2407 | 2773 |
| Threshold value = Average − 3 $\sigma$ (RLUs) | 627 | 2162 | 2559 |

Analysis Mode 2: Two Threshold Values

TABLE 10b

Responses of the SDC, PVC and RVC controls (average response, standard deviation, minimum and maximum value, threshold values)

|  | SDC | PVC | RVC |
|---|---|---|---|
| Average response (RLUs) | 998 | 2623 | 3200 |
| Standard deviation ($\sigma$) (RLUs) | 124 | 154 | 214 |
| Variation coefficient (CV) in % | 12.4% | 5.9% | 6.7% |
| Maximum of the population (RLUs) | 1246 | 2997 | 3535 |
| Minimum of the population (RLUs) | 798 | 2407 | 2773 |
| Value (threshold+) = Average − 3 $\sigma$ (RLUs) | 627 | 2162 | 2559 |
| Value (threshold+) = Average + 3 $\sigma$ (RLUs) | 1368 | 3084 | 3841 |

By combining the responses of the SDC, PVC, RVC controls and the calculated threshold values (cf. table 10a and 10b), the SDC, PVC and RVC ratios are calculated for each sample (cf. table 11a and 11b).

Analysis Mode 1: A Single Threshold Value

TABLE 11a

Responses of the SDC, PVC and RVC controls in RLUs and ratios of a population of 22 samples.

| Spec. No. | SDC RLUs | SDC ratio | Status SDC VALID/NOT VALID | PVC RLUs | PVC Ratio | Status PVC VALID/NOT VALID | RVC RLUs | RVC Ratio | Status RVC VALID/NOT VALID | Status SDC AND PVC AND RVC VALID/NOT VALID |
|---|---|---|---|---|---|---|---|---|---|---|
| 1 | 974 | 1.55 | VALID | 2997 | 1.39 | VALID | 3368 | 1.32 | VALID | VALID |
| 2 | 970 | 1.55 | VALID | 2407 | 1.11 | VALID | 3437 | 1.34 | VALID | VALID |
| 3 | 863 | 1.38 | VALID | 2489 | 1.15 | VALID | 2773 | 1.08 | VALID | VALID |
| 4 | 1072 | 1.71 | VALID | 2724 | 1.26 | VALID | 3216 | 1.26 | VALID | VALID |
| 5 | 1246 | 1.99 | VALID | 2830 | 1.31 | VALID | 3340 | 1.31 | VALID | VALID |

TABLE 11a-continued

Responses of the SDC, PVC and RVC controls in RLUs and ratios of a population of 22 samples.

| | SDC | | | PVC | | | RVC | | | Status SDC AND PVC AND RVC |
|---|---|---|---|---|---|---|---|---|---|---|
| Spec. No. | SDC RLUs | SDC ratio | Status SDC VALID/NOT VALID | PVC RLUs | PVC Ratio | Status PVC VALID/NOT VALID | RVC RLUs | RVC Ratio | Status RVC VALID/NOT VALID | VALID/NOT VALID |
| 6 | 1219 | 1.94 | VALID | 2617 | 1.21 | VALID | 3165 | 1.24 | VALID | VALID |
| 7 | 1002 | 1.60 | VALID | 2743 | 1.27 | VALID | 3535 | 1.38 | VALID | VALID |
| 8 | 1172 | 1.87 | VALID | 2670 | 1.24 | VALID | 3150 | 1.23 | VALID | VALID |
| 9 | 835 | 1.33 | VALID | 2686 | 1.24 | VALID | 3082 | 1.20 | VALID | VALID |
| 10 | 932 | 1.49 | VALID | 2575 | 1.19 | VALID | 2806 | 1.10 | VALID | VALID |
| 11 | 1061 | 1.69 | VALID | 2641 | 1.22 | VALID | 3274 | 1.28 | VALID | VALID |
| 12 | 929 | 1.48 | VALID | 2617 | 1.21 | VALID | 3200 | 1.25 | VALID | VALID |
| 13 | 1098 | 1.75 | VALID | 2495 | 1.15 | VALID | 3445 | 1.35 | VALID | VALID |
| 14 | 996 | 1.59 | VALID | 2551 | 1.18 | VALID | 3382 | 1.32 | VALID | VALID |
| 15 | 876 | 1.40 | VALID | 2732 | 1.26 | VALID | 3459 | 1.35 | VALID | VALID |
| 16 | 896 | 1.43 | VALID | 2623 | 1.21 | VALID | 3310 | 1.29 | VALID | VALID |
| 17 | 897 | 1.43 | VALID | 2429 | 1.12 | VALID | 3219 | 1.26 | VALID | VALID |
| 18 | 798 | 1.27 | VALID | 2611 | 1.21 | VALID | 2977 | 1.16 | VALID | VALID |
| 19 | 906 | 1.44 | VALID | 2440 | 1.13 | VALID | 2993 | 1.17 | VALID | VALID |
| 20 | 1007 | 1.61 | VALID | 2412 | 1.12 | VALID | 2894 | 1.13 | VALID | VALID |
| 21 | 1093 | 1.74 | VALID | 2868 | 1.33 | VALID | 3294 | 1.29 | VALID | VALID |
| 22 | 1108 | 1.77 | VALID | 2547 | 1.18 | VALID | 3083 | 1.20 | VALID | VALID |

Analysis Mode 2: Two Threshold Values

TABLE 11b

Responses of the SDC, PVC and RVC controls in RLUs and (threshold+) ratios, (threshold−) ratios of a population of 22 samples.

| | SDC | | | PVC | | | RVC | | |
|---|---|---|---|---|---|---|---|---|---|
| Spec. No. | SDC RLUs | SDC ratio (threshold−) | SDC ratio (threshold+) | PVC RLUs | PVC Ratio (threshold−) | PVC Ratio (threshold+) | RVC RLUs | RVC Ratio (threshold−) | RVC Ratio (threshold+) |
| 1 | 974 | 1.55 | 0.71 | 2997 | 1.39 | 0.97 | 3368 | 1.32 | 0.88 |
| 2 | 970 | 1.55 | 0.71 | 2407 | 1.11 | 0.78 | 3437 | 1.34 | 0.89 |
| 3 | 863 | 1.38 | 0.63 | 2489 | 1.15 | 0.81 | 2773 | 1.08 | 0.72 |
| 4 | 1072 | 1.71 | 0.78 | 2724 | 1.26 | 0.88 | 3216 | 1.26 | 0.84 |
| 5 | 1246 | 1.99 | 0.91 | 2830 | 1.31 | 0.92 | 3340 | 1.31 | 0.87 |
| 6 | 1219 | 1.94 | 0.89 | 2617 | 1.21 | 0.85 | 3165 | 1.24 | 0.82 |
| 7 | 1002 | 1.60 | 0.73 | 2743 | 1.27 | 0.89 | 3535 | 1.38 | 0.92 |
| 8 | 1172 | 1.87 | 0.86 | 2670 | 1.24 | 0.87 | 3150 | 1.23 | 0.82 |
| 9 | 835 | 1.33 | 0.61 | 2686 | 1.24 | 0.87 | 3082 | 1.20 | 0.80 |
| 10 | 932 | 1.49 | 0.68 | 2575 | 1.19 | 0.83 | 2806 | 1.10 | 0.73 |
| 11 | 1061 | 1.69 | 0.78 | 2641 | 1.22 | 0.86 | 3274 | 1.28 | 0.85 |
| 12 | 929 | 1.48 | 0.68 | 2617 | 1.21 | 0.85 | 3200 | 1.25 | 0.83 |
| 13 | 1098 | 1.75 | 0.80 | 2495 | 1.15 | 0.81 | 3445 | 1.35 | 0.90 |
| 14 | 996 | 1.59 | 0.73 | 2551 | 1.18 | 0.83 | 3382 | 1.32 | 0.88 |
| 15 | 876 | 1.40 | 0.64 | 2732 | 1.26 | 0.89 | 3459 | 1.35 | 0.90 |
| 16 | 896 | 1.43 | 0.65 | 2623 | 1.21 | 0.85 | 3310 | 1.29 | 0.86 |
| 17 | 897 | 1.43 | 0.66 | 2429 | 1.12 | 0.79 | 3219 | 1.26 | 0.84 |
| 18 | 798 | 1.27 | 0.58 | 2611 | 1.21 | 0.85 | 2977 | 1.16 | 0.78 |
| 19 | 906 | 1.44 | 0.66 | 2440 | 1.13 | 0.79 | 2993 | 1.17 | 0.78 |
| 20 | 1007 | 1.61 | 0.74 | 2412 | 1.12 | 0.78 | 2894 | 1.13 | 0.75 |
| 21 | 1093 | 1.74 | 0.80 | 2868 | 1.33 | 0.93 | 3294 | 1.29 | 0.86 |
| 22 | 1108 | 1.77 | 0.81 | 2547 | 1.18 | 0.83 | 3083 | 1.20 | 0.80 |

The status of the interpretations from the (threshold+) and (threshold−) ratios of the SDC; PVC, RVC controls is "Valid" for all 22 samples. The status of the interpretations from the SDC, PVC, RVC controls is "Valid" for all 22 samples.

A case study of methods done in downgraded mode is illustrated in tables 12 and 13a and 13b. Six cases are presented:
Case 1=absence of sample deposition.
Case 2=absence of additive deposition.
Case 3=absence of conjugates 1 deposition.
Case 4=absence of conjugates 2 deposition.
Case 5=absence of S-POD deposition.
Case 6=absence of Luminol deposition.

Analysis Mode 1: A Single Threshold Value

Cases 1 and 4 lead to SDC ratios lower than 1, which makes it possible to invalidate the measurements from these downgraded methods.

Cases 2 and 3 lead to PVC ratios lower than 1, which makes it possible to invalidate the measurements from these downgraded methods.

Cases 5 and 6 lead to SDC, PVC and RVC ratios lower than 1, which makes it possible to invalidate the measurements from these downgraded methods. The RUC signal makes it possible to specifically invalidate the developing step (S-POD deposition and Luminol deposition). However, the invalidation of the procedure by a RVC ratio lower than 1 implies an absence of the systematic signal of the SDC and PVC controls (indicated with "*" in table 9). In this case, it is not possible to determine whether the depositions of the sample and the conjugates 2 (depositions controlled by SDC) or the depositions of additive and the conjugates 1 (depositions controlled by PVC) have taken place correctly.

Analysis Mode 2: Two Threshold Values

Cases 1 and 4 lead to SVC (threshold−) ratios lower than 1, which makes it possible to invalidate the measurements from these downgraded methods. In addition to case 1, the PVC (threshold+) ratio is greater than 1, which reflects an indirect impact of the absence of sample on the PVC control.

Cases 2 and 3 lead to PVC (threshold−) ratios lower than 1, which makes it possible to invalidate the measurements from these downgraded methods.

Cases 5 and 6 lead to SDC, PVC and RVC (threshold−) ratios lower than 1, which makes it possible to invalidate the measurements from these downgraded methods. The RVC signal makes it possible to specifically invalidate the developing step (S-POD deposition and Luminol deposition). However, the invalidation of the procedure by a RVC (threshold−) ratio lower than 1 implies an absence of the systematic signal of the SDC and PVC controls (indicated with "h" in table 9). In this case, it is not possible to determine whether the depositions of the sample and the conjugates 2 (depositions controlled by SDC) or the depositions of additive and the conjugates 1 (depositions controlled by PVC) have taken place correctly.

TABLE 12

Detail of the 6 downgraded method cases

| | Step 1 | | | Step 2 | Step 3 | Step 4 |
|---|---|---|---|---|---|---|
| Case | Sample Volume (µL) | Additive Volume (µL) | Conjugates 1 Volume (µL) | Conjugates 2 Volume (µL) | S-POD Volume (µL) | Volume Luminol (µL) |
| 1 | 0 | 20 | 20 | 50 | 50 | 50 |
| 2 | 40 | 0 | 20 | 50 | 50 | 50 |
| 3 | 40 | 20 | 0 | 50 | 50 | 50 |
| 4 | 40 | 20 | 20 | 0 | 50 | 50 |
| 5 | 40 | 20 | 20 | 50 | 0 | 50 |
| 6 | 40 | 20 | 20 | 50 | 50 | 0 |

Analysis Mode 1: A Single Threshold Value

TABLE 13a

Responses of the SDC, PVC and RVC controls in RLU and ratio of a population of 22 samples

| | SDC | | | PVC | | | RVC | | | SDC AND PVC AND |
|---|---|---|---|---|---|---|---|---|---|---|
| Case | SDC RLUs | SDC ratio | SDC VALID/ NOT VALID (NV) | PVC RLUs | PVC Ratio | PVC VALID/ NOT VALID (NV) | RVC RLUs | RVC Ratio | RVC VALID/ NOT VALID (NV) | RVC VALID/ NOT VALID (NV) |
| 1 | 37 | 0.06 | NV | 3939 | 1.82 | VALID | 3458 | 1.35 | VALID | NV |
| 2 | 991 | 1.58 | VALID | 72 | 0.03 | NV | 3569 | 1.39 | VALID | NV |
| 3 | 983 | 1.57 | VALID | 59 | 0.03 | NV | 3046 | 1.19 | VALID | NV |
| 4 | 18 | 0.03 | NV | 2727 | 1.26 | VALID | 3655 | 1.43 | VALID | NV |
| 5 | 5 | 0.01 | NV | 4 | 0.00 | NV | 5 | 0.00 | NV | NV |
| 6 | 6 | 0.01 | NV | 7 | 0.00 | NV | 5 | 0.00 | NV | NV |

Analysis Mode 2: Two Threshold Values

TABLE 13b

Responses of the SDC, PVC and RVC controls in RLU and ratio of a population of 22 samples

| | SDC | | | | PVC | | | | RVC | | | |
|---|---|---|---|---|---|---|---|---|---|---|---|---|
| Case | SDC RLUs | SDC ratio (threshold−) | SDC ratio (threshold+) | SDC VALID/ NOT VALID (NV) | PVC RLUs | PVC Ratio (threshold−) | PVC Ratio (threshold+) | PVC VALID/ NOT VALID (NV) | RVC RLUs | RVC Ratio (threshold−) | RVC Ratio (threshold+) | RVC VALID/ NOT VALID (NV) | SDC AND PVC AND RVC VALID/NOT VALID (NV) |
| 1 | 37 | 0.06 | 0.03 | NV | 3939 | 1.82 | 1.28 | NV | 3458 | 1.35 | 0.90 | VALID | NV (direct measurement), NV (indirect measurement of the effect of the absence of sample on PVC) |

TABLE 13b-continued

Responses of the SDC, PVC and RVC controls in RLU and ratio of a population of 22 samples

| | SDC | | | | PVC | | | | RVC | | | | |
|---|---|---|---|---|---|---|---|---|---|---|---|---|---|
| Case | SDC RLUs | SDC ratio (threshold−) | SDC ratio (threshold+) | SDC VALID/ NOT VALID (NV) | PVC RLUs | PVC Ratio (threshold−) | PVC Ratio (threshold+) | PVC VALID/ NOT VALID (NV) | RVC RLUs | RVC Ratio (threshold−) | RVC Ratio (threshold+) | RVC VALID/ NOT VALID (NV) | SDC AND PVC AND RVC VALID/NOT VALID (NV) |
| 2 | 991 | 1.58 | 0.72 | VALID | 72 | 0.03 | 0.02 | NV | 3569 | 1.39 | 0.93 | VALID | NV |
| 3 | 983 | 1.57 | 0.72 | VALID | 59 | 0.03 | 0.02 | NV | 3046 | 1.19 | 0.79 | VALID | NV |
| 4 | 18 | 0.03 | 0.01 | NV | 2727 | 1.26 | 0.88 | VALID | 3655 | 1.43 | 0.95 | VALID | NV |
| 5 | 5 | 0.01 | 0.00 | NV | 4 | 0.00 | 0.00 | NV | 5 | 0.00 | 0.00 | NV | NV |
| 6 | 6 | 0.01 | 0.00 | NV | 7 | 0.00 | 0.00 | NV | 5 | 0.00 | 0.00 | NV | NV |

Furthermore, by comparing the RLU signals obtained between a MPX format without SDC or PVC versus a MPX format with SDC and PVC, it appears that the addition of SDC and PVC tests does not affect the performance of a multiplex including 4 analytes to be assayed (i.e., the deviations in % between the RLU signals of a MPX format without SDC or PVC versus a MPX format with SDC and PVC are comprised in an interval +/−20%, which is considered statistically acceptable).

The invention claimed is:

1. A solid support appropriate for a multiplex analysis of at least one sample, said solid support comprising at least one compartment,
   said compartment comprising a plurality of spots, each spot being deposited at a separate location within said at least one compartment,
   said plurality of spots comprising two or more control spots deposited upon said solid support within said at least one compartment and at least two detection spots comprising a ligand specific for an analyte in a sample,
   and said at least two control spots being selected from the group consisting of a spot for controlling the deposition of a sample, a spot for controlling the deposition of an analyte detection ligand and a spot for controlling the deposition of a reporter, wherein:
   a) the spot for controlling the deposition of the sample comprises at least one control capture ligand specific for a control compound naturally present in the sample to be analyzed, said control capture ligand being an antibody, antigen, peptide, carbohydrate, lipid, or nucleic acid;
   b) the spot for controlling the deposition of the detection ligand for the analyte comprises at least one additive capture ligand specific for an additive that is added to a sample and said additive is not naturally present in the sample or derived from any compound present in the sample, said at least one additive capture ligand being an antibody, antigen, peptide, carbohydrate, lipid, or nucleic acid;
   c) the spot for controlling the deposition of the reporter comprises a direct marker, an indirect marker or a carrier molecule coupled to an indirect marker, wherein the reporter specifically interacts with the indirect marker or the indirect marker coupled to the carrier molecule, optionally, in presence of a substrate, to produce a detectable signal,
   said direct marker being selected from a radioisotope, a fluorochrome, a lanthanide, a luminescent compound, a transition metal, and colored, fluorescent or luminescent nanoparticles,
   said indirect marker being an enzyme, biotin, avidin, streptavidin, neutravidin, a hapten, an antigen or an antibody,
   said carrier being a polypeptide, functionalized polymer, a copolymer, or an antibody, and
   said reporter being an enzymatic substrate for an enzyme, an enzyme for a luminescent compound, and avidin, streptavidin, or neutravidin coupled to a direct or indirect marker for biotin, and
   said ligands for analyte detection are antibodies, antigens, peptides, carbohydrates, lipids, or nucleic acids.

2. The solid support according to claim 1, wherein one of the control spots is the spot for controlling the deposition of the sample.

3. The solid support according to claim 1, wherein one of the control spots is the spot for controlling the deposition of the reporter.

4. The solid support according to claim 1, wherein one of the control spots is the spot for controlling the deposition of the detection ligand of the analyte.

5. The solid support according to claim 1, wherein the compartment comprises the spot for controlling the deposition of the sample and the spot for controlling the deposition of the detection ligand for the analyte.

6. The solid support according to claim 2, wherein the compartment comprises the spot for controlling the deposition of the sample and the spot for controlling the deposition of the reporter.

7. The solid support according to claim 3, wherein the compartment comprises the spot for controlling the deposition of the detection ligand for the analyte and the spot for controlling the deposition of the reporter.

8. The solid support according to claim 1, said compartment comprising the spot for controlling the deposition of the sample; the spot for controlling the deposition of the detection ligand for the analyte; and the spot for controlling the deposition of the reporter.

9. The solid support according to claim 1, wherein the at least one control capture ligand is an antibody specific to the control compound and the at least one additive capture ligand is an antibody specific to the additive.

10. The solid support according to claim 9, wherein the at least one control capture ligand is an antibody specific to the control compound, the at least one additive capture ligand is an antibody specific to the additive, and the analyte detection ligand is an antibody specific for the analyte.

11. The solid support according to claim 1, wherein the spots are cylindrical.

12. The solid support according to claim 1, wherein the spots are discoid.

* * * * *